United States Patent [19]

Beck et al.

[11] Patent Number: 4,666,504

[45] Date of Patent: May 19, 1987

[54] POLLEN FORMATION INHIBITING 1-PHENYL-4-CARBOXY-5-PYRAZOLECARBOXAMIDES

[75] Inventors: James R. Beck, Indianapolis; Carole W. Price, Greenfield, both of Ind.

[73] Assignee: Eli Lilly and Company, Indianapolis, Ind.

[21] Appl. No.: 762,732

[22] Filed: Aug. 5, 1985

Related U.S. Application Data

[63] Continuation-in-part of Ser. No. 654,061, Sep. 25, 1984, abandoned.

[51] Int. Cl.$^4$ .................... A01N 43/56; C07D 231/14
[52] U.S. Cl. .......................................... 71/92; 548/378
[58] Field of Search .............................. 548/378; 71/92

[56] References Cited

U.S. PATENT DOCUMENTS

| | | | |
|---|---|---|---|
| 4,134,987 | 1/1979 | Huppatz | 548/378 |
| 4,147,528 | 4/1979 | McNulty et al. | 71/92 |
| 4,238,220 | 12/1980 | Carlson | 71/94 |
| 4,345,934 | 8/1982 | Fujimoto | 71/92 |

FOREIGN PATENT DOCUMENTS

| | | | |
|---|---|---|---|
| 49971 | 4/1982 | European Pat. Off. | 544/239 |
| 493458 | 7/1980 | Spain | 548/378 |

OTHER PUBLICATIONS

C.A. 85, 45873h (1976).
C.A. 74, 2483m (1971).
C.A. 84, 165291t (1976).
C.A. 70, 37710c (1969).
C.A. 98, 72004a (1983).
C.A. 84, 90494a (1976).
C.A. 67, 90758p (1967).

*Primary Examiner*—John M. Ford
*Assistant Examiner*—Kurt G. Briscoe
*Attorney, Agent, or Firm*—Joseph A. Jones; Leroy Whitaker

[57] ABSTRACT

Pollen formation in cereal grain plants is inhibited by application of a 4-carboxy(or derivative)-1-aryl-5-pyrazolecarboxamide. Production of hybrid seed is facilitated by use of the compounds.

64 Claims, No Drawings

POLLEN FORMATION INHIBITING 1-PHENYL-4-CARBOXY-5-PYRAZOLECARBOXAMIDES

Cross-Reference

This application is a continuation-in-part of copending application Ser. No. 06/654,061, filed Sept. 25, 1984, now abandoned.

FIELD OF THE INVENTION

This invention belongs to the fields of plant hybridization and organic chemistry, particularly, agricultural chemistry. Very important improvements in the hardiness and yield of cultivated plants, particularly grains, have been made by the technique of hybridization. In the past, hybridizing those species, in which each plant produces both pollen and pollen receiving organs, has been very difficult.

Compounds have been found which are capable of inhibiting formation of pollen. The use of such a compound greatly simplifies hybridization. Plants of the two strains to be crossed are simply planted adjacent to one another, as in long, relatively narrow plots, and the plots of one of the strains are treated with a pollen formation inhibitor. All of the seed produced by the treated plants will be hybrid seed, originating from pollen contributed by the untreated plants, if the pollen formation inhibitor is perfectly effective.

Compounds having pollen formation inhibiting activity have been taught in the past by Fujimoto, U.S. Pat. No. 4,345,934, by McNulty and Warner, U.S. Pat. No. 4,147,528, and by Carlson, U.S. Pat. No. 238,220.

SUMMARY OF THE INVENTION

The present invention provides the pollen formation inhibiting pyrazoles of the formula

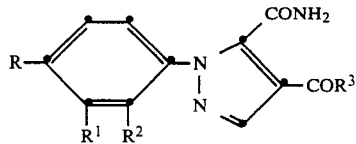

wherein R, $R^1$ and $R^2$ independently represent chloro, bromo, fluoro, $C_1$–$C_3$ alkoxy, $C_1$–$C_4$ alkyl or hydrogen, provided that at least one of R, $R^1$ and $R^2$ represents hydrogen, and further provided that $R^2$ may represent a group other than hydrogen only when one of R and $R^1$, but not both, represents a group other than hydrogen; $R^3$ represents hydroxy, methoxy, ethoxy, allyloxy or a phytologically-acceptable moiety forming a salt of the carboxylic acid.

The invention also provides pollen formation inhibiting compositions which comprise a compound of the above formula and one or more phytologically-acceptable diluents. The invention also provides a method of inhibiting pollen formation in a cereal grain plant which is sensitive to such treatment comprising supplying to the plant at a time prior to another formation a pollen formation inhibiting amount of a compound of the above formula.

Further, the invention provides a method of producing hybrid cereal grain seed having a male and a female parent variety, comprising planting seed of said male and female parent varieties in separate plots adjacent to each other, treating the female parent plants growing from said female parent seed with a pollen formation inhibiting method as just described, said female parent variety being sensitive to such treatment, allowing said treated female parent plants to be pollinated by the male parent plants growing from said male parent seed and to produce hybrid seed, and harvesting said hybrid seed from the treated female parent plants.

DESCRIPTION OF THE PREFERRED EMBODIMENTS

In this document, all temperatures are described in degrees Celsius. All expressions of percentage, proportion and the like are in weight units unless otherwise stated.

In the above formula, the terms $C_1$–$C_2$ and $C_1$–$C_4$ alkyl include such groups as methyl, ethyl, propyl, isopropyl, butyl, t-butyl and isobutyl, and the terms $C_1$–$C_2$ and $C_1$–$C_3$ alkoxy include such groups as methyl, ethyl, propyl and isopropyl linked through an oxygen atom.

The salts of the above formula are formed with any phytologically-acceptable moiety capable of forming a salt of the carboxylic acid. The preferred saltforming moieties include alkali metals, amine groups, and quaternary ammonium groups. More particularly, sodium, potassium, lithium, $C_1$–$C_4$ alkylamino, dialkylamino and trialkylamino groups and quaternary ammonium groups wherein the nitrogen atom is substituted with four hydrogen, $C_1$–$C_4$ alkyl, phenyl or benzyl moieties are more highly preferred.

For example, quaternary ammonium groups such as ammonium, tetramethyl ammonium, diethyl-dimethyl ammonium, diethyl-dibutyl ammonium, benzyl-trimethyl ammonium, t-butyl-trimethyl ammonium, phenyl-triethyl ammonium, diethyl-dipropyl ammonium, s-butyl-trimethyl ammonium, isobutyl-triethyl ammonium and the like are useful and may be chosen for convenience in the circumstances. Further, such amines as methylamine, butylamine, triethylamine, dipropylamine and the like are convenient for salt formation.

Certain classes of the compounds of the present invention are particularly preferred. One such class includes the carboxylic acids wherein $R^3$ is hydroxy, and salts thereof. Another preferred class includes compounds wherein $R^1$ is a group other than hydrogen, and R and $R^2$ are hydrogen. Another preferred class includes compounds wherein R and $R^1$ independently represent chloro, bromo, methoxy, ethyl or methyl. Still another preferred class includes the compounds wherein R and $R^2$ are hydrogen and $R^1$ is chloro, bromo, fluoro, $C_1$–$C_2$ alkyl or $C_1$–$C_2$ alkoxy; a more preferred class includes such compounds wherein $R^1$ is chloro, ethyl, methyl or methoxy; and another more preferred class includes such compounds wherein $R^1$ is chloro, bromo or methyl.

The following group of exemplary compounds of the present invention are mentioned to assure that the reader fully understands the invention.

4-carboxy-1-(3-propylphenyl)-5-pyrazolecarboxamide;
1-(4-ethylphenyl)-4-methoxycarbonyl-5-pyrazolecarboxamide;
1-(2,4-dibromophenyl)-4-ethoxycarbonyl-5-pyrazolecarboxamide;
4-allyloxycarbonyl-1-(2,3-difluorophenyl)-5-pyrazolecarboxamide;
4-carboxy-1-(3,4-diethylphenyl)-5-pyrazolecarboxamide, benzyl-trimethylammonium salt;

4-carboxy-1-(4-isopropyl-2-methylphenyl)-5-pyrazolecarboxamide, phenyl-triethylammonium salt;
4-carboxy-1-(3-isobutylphenyl)-5-pyrazolecarboxamide;
1-(4-butylphenyl)-4-ethoxycarbonyl-5-pyrazolecarboxamide;
1-(3-t-butylphenyl)-4-methoxycarbonyl-5-pyrazolecarboxamide;
4-carboxy-1-[3-(1-methylpropyl)phenyl]-5-pyrazolecarboxamide;
4-carboxy-1-(4-methyl-3-propylphenyl)-5-pyrazolecarboxamide, tetrapropylammonium salt;
4-carboxy-1-(3-isopropyl-4-propylphenyl)-5-pyrazolecarboxamide, trimethylamine salt;
1-(3-bromo-2-chlorophenyl)-4-carboxy-5-pyrazolecarboxamide, diethyl-dipropylammonium salt;
1-(4-bromo-3-propylphenyl)-4-carboxy-5-pyrazolecarboxamide, diphenyl-dimethylammonium salt;
1-(2-bromo-4-methylphenyl)-4-carboxy-5-pyrazolecarboxamide, benzyl-triethylammonium salt;
1-(3-bromo-4-methylphenyl)-4-carboxy-5-pyrazolecarboxamide;
4-carboxy-1-(4-fluoro-3-methylphenyl)-5-pyrazolecarboxamide;
4-carboxy-1-(4-ethyl-2-fluorophenyl)-5-pyrazolecarboxamide, lithium salt;
4-carboxy-1-(3,4-difluorophenyl)-5-pyrazolecarboxamide, tetra(isobutyl)ammonium salt;
4-carboxy-1-(2-propyl-4-fluorophenyl)-5-pyrazolecarboxamide, butyl-trimethylammonium salt;
4-carboxy-1-(3-ethoxyphenyl)-5-pyrazolecarboxamide, sodium salt;
4-methoxycarbonyl-1-(4-propoxyphenyl)-5-pyrazolecarboxamide;
1-(3-isopropoxyphenyl)-4-methoxycarbonyl-5-pyrazolecarboxamide; and
4-carboxy-1-(3-methoxyphenyl)-5-pyrazolecarboxamide, potassium salt.

The compounds of the present invention are prepared by a basic process whose first step is the reaction of an aryl hydrazine with an alkyl (alkoxymethylene)cyanoacetate to prepare the corresponding 1-phenyl-5-amino-1H-4-pyrazolecarboxylate. Next, the aminopyrazole is converted to the corresponding 5-halopyrazolecarboxylate, which is then converted to the 5-cyanopyrazolecarboxylate. That compound is the key intermediate for the preparation of the present pollen formation inhibitors.

In the final step of the basic process, the 5-cyano-4-pyrazolecarboxylate is hydrolyzed with a strong base, preferably with potassium hydroxide, to prepare the desired 4-carboxy-5-pyrazolecarboxamide. The reaction scheme is illustrated below.

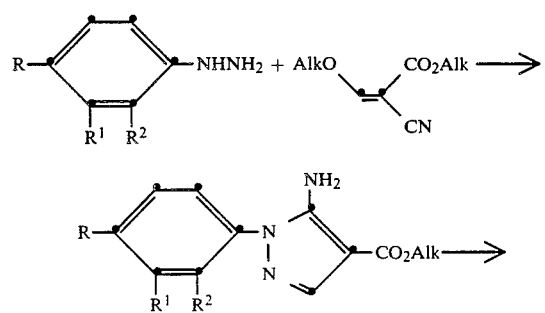

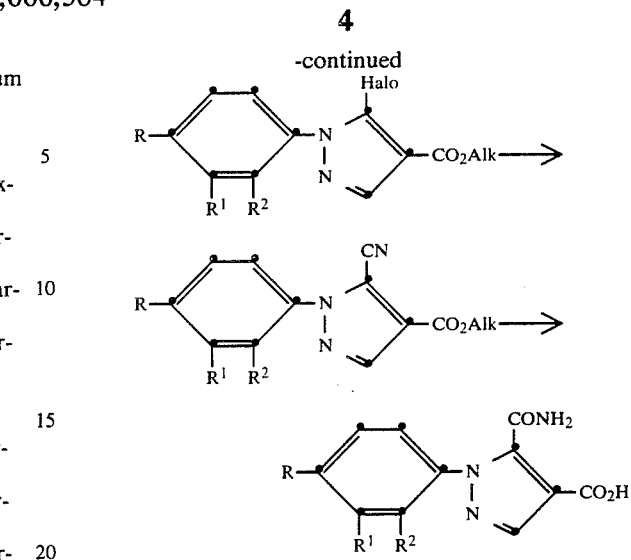

In the above scheme, the term Alk refers to $C_1$-$C_4$ alkyl groups, and the term Halo refers to chloro or bromo.

All of the steps of the processes described in this document proceed in acceptable yields without the use of unusual excess quantities of any reactant. In general, equimolar quantities can be used with satisfactory results. However, as is usual in organic reactions, it is preferable and advisable to use an excess amount of reactants which are inexpensive or easy to obtain, in order to assure full utilization of reactants which are expensive or difficult to obtain. Similarly, the steps of the process may be allowed to proceed for a long period of time, to maximize yield of the desired product, or may be halted before the reaction is complete, to maximize throughput of product from the system. Either manner of operating a process may be preferable, depending on the circumstances.

In the first step of the above scheme, it is most preferred to use aqueous acetic acid as the reaction solvent. An inorganic acetate salt in the reaction mixture is also beneficial, in some cases. However, the reaction of the hydrazine with the cyanoacetate may also be carried out in any suitable organic solvent, particularly a lower alkanol such as methanol or ethanol. The preferred reaction temperature is elevated, in the range of about 50°–150°. It will be understood that temperatures above the boiling point of the reaction mixture may be used at elevated pressures. However, the reactions will go at any reasonable temperature, such as about 0°–200°, if appropriate operating care is used.

The halogenation step of the above scheme is preferably carried out with nitrosyl chloride as both the diazotizing and halogenating agent, resulting in a 5-chloropyrazole. It is conventional to use nitrosyl chloride as a gas, by bubbling it through the vigorously mixed reaction mixture. The present chlorination is carried out in any non-reactive organic solvent, most preferably in a halogenated alkane such as chloroform, carbon tetrachloride and the like. Moderate temperatures in the range of 0°–50° are preferred, in order to maximize the solubility of nitrosyl chloride in the reaction mixture.

5-Bromopyrazole intermediates are prepared with an alkyl nitrite as the diazotizing agent, and an appropriate halogen source. Isoamyl nitrite, t-butyl nitrite and the like are appropriate diazotizing agents, and bromoform and elemental bromine are convenient sources of bromine. The reaction conditions are substantially the same as those for chlorinations.

Cyanation of the 5-halopyrazole is carried out in a conventional manner with an alkali metal cyanide, such as sodium cyanide, lithium cyanide or potassium cyanide. The cyanation can be done in inert organic solvents of which aprotic solvents are preferred. For example, dimethylformamide, dimethylsulfoxide and hexamethylphosphoramide are particularly preferred solvents in this step. It is preferred to cyanate at elevated temperatures in the range of about 50°-200°, most preferably about 80°-140°.

The hydrolysis step, which prepares the 4-carboxy-5-pyrazolecarboxamide, is most conveniently carried out with potassium hydroxide in aqueous ethanol. Conventionally, the base is dissolved in a minimum amount of water, and added to ethanol to prepare the reaction medium. Other alkali metal hydroxides, such as sodium hydroxide and lithium hydroxide, are also useful for the process. Similarly, other reaction solvents besides aqueous ethanol are useful, particularly other aqueous alkanols such as methanol, propanol and isopropanol. The hydrolysis is preferably carried out at a moderately elevated temperature in the range of about 50°-100°, most preferably at the reflux temperature of the reaction mixture.

An improved method of preparing certain alkylaryl hydrazines, particularly 3-methyl- and 3-ethylphenylhydrazines, is carried out by reacting the corresponding aniline with sodium nitrite to prepare the diazonium salt, and reacting the salt with potassium sulfite as described in Houben-Weyl, Methoden der Organische Chemie, Vol. 10/2, p. 180 (1967). The preparations below illustrate the preparation of an aryl hydrazine by the process just described.

Should one not want to use an alkyl (alkoxymethylene)cyanoacetate in the cyclization, the pyrazole can also be formed by reacting the aryl hydrazine with a dialkyl alkoxymethylenemalonate under basic conditions in an aqueous reaction mixture such as aqueous ethanol. Such a cyclization prepares a pyrazole having a hydroxy group at the 5-position and an alkoxycarbonyl at the 4-position. The next step in such a sequence is to hydrolyze the hydroxypyrazole in an acid environment such as acidic alcohol, which step removes the alkoxycarbonyl group. The resulting intermediate is then reacted with a Vilsmeier reagent to replace the hydroxy group with a chlorine atom, and, simultaneously, to insert a formyl group at the 4-position. The formyl is converted to an alkoxycarbonyl by reaction in an alkanol with hydrogen peroxide in the presence of sulfuric acid. The resulting product is a 5chloro-4-alkoxycarbonylpyrazole, which is converted to the nitrile as described in the basic process discussed above.

Salts of the 4-carboxy-5-pyrazolecarboxamides are readily prepared in the usual ways, as by contacting the compound with the appropriate base in an aqueous alkanol or aqueous ketone. When an alkali metal salt is desired, the base can be any appropriate alkali metal hydroxide, alkoxide, carbonate or bicarbonate. When a quaternary ammonium salt is to be made, the appropriate quaternary ammonium halide, sulfonate, hydroxide, methanesulfonate or the like is combined with the acid in a suitable organic solvent. Salts are formed at moderate temperatures in the range of 0°-100°.

Compounds wherein the 4-carboxy group has been esterified are easily prepared in the usual manner, by reacting the 4-carboxy compound with methanol, allyl alcohol or ethanol in an organic solvent, preferably in the presence of a small amount of a mineral acid as esterification catalyst. Esters are also prepared by reacting an alkali metal salt of the acid with an allyl, methyl or ethyl halide. Moderate temperatures in the range of 50°-100° are quite satisfactory, and the reaction times are usually brief. Coupling agents may be used to assist esterifications but are not usually necessary.

The following Preparations and Examples are shown further to assist the reader in preparing the compounds of the present invention.

EXAMPLE 1

4-Carboxy-1-(3-chlorophenyl)-5-pyrazolecarboxamide.

To a 22-liter flask equipped with a heating mantle and condenser were added 2 L. of deionized water, 7.55 L. of acetic acid, 1.37 kg. of sodium acetate, 1.923 kg. of 3-chlorophenylhydrazine hydrochloride, and 1.854 kg. of ethyl (ethoxymethylene)cyanoacetate. The mixture was slowly warmed to the reflux temperature, about 95°, and was stirred at that temperature for 4 hours. The mixture was then cooled to about 10°, adding a little more water to keep it from becoming too thick to stir. The mixture was stirred at about 10° for 1 hour and filtered. The solids were washed with water, and dried by pulling air through the filter cake on a vacuum funnel. The solids were then dissolved in 13 L. of denatured ethanol, and the solution was heated to reflux. It was filtered at elevated temperature, and was then cooled with stirring and filtered to obtain 2.195 kg. of product. The filtrate was concentrated and 170 g. of additional intermediate product was obtained in successive crystallizations, providing in total 2.365 kg. of ethyl 5-amino-1-(3-chlorophenyl)-4-pyrazolecarboxylate.

The above intermediate was dissolved in 13 L. of chloroform, and was treated by bubbling nitrosyl chloride through it at ambient temperature. The nitrosyl chloride was generated by slowly adding 1.23 kg. of sodium nitrite in aqueous solution to 7.2 L. of concentrated hydrochloric acid. The addition of the nitrite was controlled so that its addition took 2 hours, and the maximum temperature of the reaction mixture was 35°. The mixture was stirred at ambient temperature for 1 hour after the nitrosyl chloride generation was complete, and then the mixture was heated to reflux and stirred at that temperature for one hour. It was then cooled, stirred overnight, dried with sodium sulfate, and filtered. The solvent was removed under vacuum, and the solids were crystallized from denatured ethanol to obtain 2.002 kg. of ethyl 5-chloro-1-(3-chlorophenyl)-4-pyrazolecarboxylate.

The above intermediate was dissolved in 13 L. of anhydrous dimethylformamide, and to it was added 686 g. of anhydrous sodium cyanide. The mixture was stirred at 100° for 4 hours, and then was cooled overnight at ambient temperature with stirring. It was then added in portions with stirring to 40 L. of ice-water. The aqueous mixture was stirred for about 45 minutes and filtered, and the solids were washed several times with water. The solids were then recrystallized from anhydrous ethanol to obtain 1.591 kg. of ethyl 1-(3-chlorophenyl)-5-cyano-4-pyrazolecarboxylate.

A 1.445 kg. portion of the above intermediate was added to 14 L. of denatured ethanol and heated to about 50°. To it was added an additional 5 L. of ethanol, 1 L. of water, and 1.035 kg. of 85% potassium hydroxide.

The mixture was stirred under reflux (76°–77°) for about 2 hours. It was then let stand overnight, cooling to ambient temperature. The mixture was then reheated to about 70° to dissolve all of the solids, and then 25–30 L. of ice and water were added, and the pH was dropped to 1–2 by the addition of concentrated hydrochloric acid. The mixture was stirred one hour at 10°, and was filtered. The solids were washed with water and dried at 50° to obtain 1.024 kg. of the desired product, m.p. 223°–225°. Its elemental analysis was as follows.

Calculated for: $C_{11}H_8N_3O_3Cl$: Theoretical: C, 49.73; H, 3.04; N, 15.82; Found: C, 49.81; H, 2.82; N, 15.61.

EXAMPLE 2

4-Carboxy-1-(3-fluorophenyl)-5-pyrazolecarboxamide.

A 5.5 g. portion of ethyl 5-cyano-1-(3-fluorophenyl)-4-pyrazolecarboxylate and 4.7 g. of potassium hydroxide were dissolved in 100 ml. of ethanol at the reflux temperature and the mixture was stirred at that temperature for 2 hours. The mixture was then diluted to 350 ml. with cold water, and was heated slightly to obtain a solution which was made acid with concentrated hydrochloric acid. The product was precipitated by adding small amounts of ice, and the precipitated product was then collected by filtration and crystallized from ethanol-water to obtain 3.6 g. of the desired product, m.p. 215°–216°, having the following elemental analysis.

Calculated for: $C_{11}H_8N_3O_3F$: Theoretical: C, 53.01; H, 3.21; N, 16.87; Found: C, 53.16; H, 3.27; N, 16.91.

EXAMPLE 3

4-Carboxy-1-phenyl-5-pyrazolecarboxamide.

A 4 g. portion of ethyl 5-cyano-1-phenyl-4-pyrazolecarboxylate was reacted with 2 g. of potassium hydroxide in 60 ml. of denatured ethanol substantially as described in Example 2, to obtain 2.7 g. of the desired product, m.p. 23°–235°, having the following elemental analysis.

Calculated for: $C_{11}H_9N_3O_3$. Theoretical: C, 57.14; H, 3.92; N, 18.17; Found: C, 57.38; H, 3.93; N, 18.37.

EXAMPLE 4

4-Carboxy-1-(4-chlorophenyl)-5-pyrazolecarboxamide.

The process of Example 2 was followed, starting with 3.7 g. of ethyl 1-(4-chlorophenyl)-5-cyano-4-pyrazolecarboxylate and 2 g. of sodium hydroxide in 60 ml. of denatured ethanol and 60 ml. of water to obtain 2.3 g. of the desired product, m.p. 249°–250°. The elemental analysis was as follows.

Calculated for: $C_{11}H_8N_3O_3Cl$: Theoretical: C, 49.73; H, 3.04; N, 15.82; Found C, 49.94; H, 3.32; N, 15.78.

EXAMPLE 5

4-Carboxy-1-(2,4-dichlorophenyl)-5-pyrazolecarboxamide.

A 2.5 g. portion of ethyl 1-(2,4-dichlorophenyl)-5-cyano-4-pyrazolecarboxylate was reacted with 1 g. of potassium hydroxide in 60 ml. of 50% aqueous ethanol to obtain 1.2 g. of purified product, m.p. 239°–240°, with the following elemental analysis.

Calculated for: $C_{11}H_7N_3O_3Cl_2$: Theoretical: C, 44.03; H, 2.35; N, 14.01; Found C, 44.05; H, 2.64; N, 13.83.

EXAMPLE 6

1-(4-Bromophenyl)-4-carboxy-5-pyrazolecarboxamide.

A 3.5 g. portion of ethyl 1-(4-bromophenyl)-5-cyano-4-pyrazolecarboxylate was reacted with 2.15 g. of potassium hydroxide in 50 ml. of ethanol under reflux for 2 hours to obtain 2.45 g. of the desired product, m.p. 251°–252.5°. The elemental analysis was as follows.

Calculated for: $C_{11}H_8N_3O_3Br$: Theoretical: C, 42.61; H, 2.60; N, 13.55; Found: C, 42.84; H, 2.72; N, 13.29.

EXAMPLE 7

4-Carboxy-1-(3,4-dichlorophenyl)-5-pyrazolecarboxamide.

Fifteen g. of ethyl 1-(3,4-dichlorophenyl)-5-cyano-4-pyrazolecarboxylate was dissolved in 200 ml. of ethanol, and 5.6 g. of potassium hydroxide was added. The reaction mixture was stirred under reflux for 1 hour, and was then poured over a large amount of ice and made acid with concentrated hydrochloric acid. The mixture was filtered, and the solids were found by nuclear magnetic resonance analysis to consist of the partially hydrolyzed 4-carboxy-5-cyanopyrazole. A 2 g. portion of that intermediate was held out for further examination, and the rest of the solids were redissolved in 200 ml. of ethanol and stirred under reflux for 18 hours with 5.6 g. of potassium hydroxide. The mixture was then poured over ice, made acid, and filtered. The solids were recrystallized from ethanol, and the mother liquor was chromatographed over a silica gel column with methanol as the eluent. The product-containing fractions were evaporated to dryness and the residues were recrystallized from methanol to obtain the desired product, m.p. 249°–250°. The elemental analysis was as follows.

Calculated for: $C_{11}H_7N_3O_3Cl_2$: Theoretical: C, 44.03; H, 2.35; N, 14.00; Found C, 43.93; H, 2.37; N, 13.91.

EXAMPLE 8

4-Carboxy-1-(4-methylphenyl)-5-pyrazolecarboxamide.

To 10 g. of ethyl 5-cyano-1-(4-methylphenyl)-4-pyrazolecarboxylate was added 5.6 g. of potassium hydroxide and 200 ml. of water followed by enough water to cause solution. The mixture was stirred under reflux for 8 hours and allowed to stand for 3 days. It was then poured over ice, made acid and filtered. The solids from the filtration were heated in 100 ml. of ethyl acetate, and the undissolved solid was separated, dried and identified as 4.25 g. of the desired product, m.p. 260° dec. The product was identified by nuclear magnetic resonance analysis in DMSOd$_6$. δ2.36 (s,3), methyl; 7.32 (d,2), aromatic; 7.45 (d,2), aromatic; 8.01 (s,1), pyrazole; 7.91 (s,1), carboxamide; 8.33 (s,1), carboxamide.

EXAMPLE 9

1-(3-Bromophenyl)-4-carboxy-5-pyrazolecarboxamide.

A 14 g. portion of ethyl 1-(3-bromophenyl)-5-cyano-4-pyrazolecarboxylate was hydrolyzed by stirring under reflux in 200 ml. of ethanol with 6 g. of potassium hydroxide for 2 hours. The mixture was then poured over ice, acidified and filtered, and the solids were crystallized from ethanol/water and dried at 168° to obtain 10 g. of the desired product, m.p. 215°–217° dec. The product was identified by NMR analysis in CDCl$_3$/DMSOd$_6$. δ7.06 (s,1), carboxamide; 7.30–7.64

(m,4), aromatic; 8.08 (s,1), pyrazole; 9.10 (s,1), carboxamide.

EXAMPLE 10

4-Carboxy-1-(3-methylphenyl)-5-pyrazolecarboxamide.

A 9 g. portion of ethyl 5-cyano-1-(3-methylphenyl)-4-pyrazolecarboxylate was dissolved in 200 ml. of ethanol, and 5.8 g. of potassium hydroxide was added. The mixture was stirred under reflux for 4 hours, and then was cooled, diluted with water and made acid. The mixture was filtered, and the solids were washed with ethyl acetate as shown above in Example 8 to obtain 3.8 g. of the desired product, m.p. 209°–211° dec. It was identified by elemental analysis.

Calculated for: $C_{12}H_{11}N_3O_3$: Theoretical: C, 58.77; H, 4.52; N, 17.13; Found: C, 58.58; H, 4.63; N, 16.85.

EXAMPLE 11

4-Carboxy-1-(4-fluorophenyl)-5-pyrazolecarboxamide.

A 2.5 g. portion of ethyl 5-cyano-1-(4-fluorophenyl)-4-pyrazolecarboxylate was combined with 2.6 g. of potassium hydroxide and stirred under reflux in 100 ml. of denatured ethanol for 4 hours. It was then cooled, made acid, diluted with water, and concentrated under vacuum to obtain 2.8 g. of the desired compound, m.p. 232° dec. after recrystallization from acetone. It was identified by elemental analysis.

Calculated for: $C_{11}H_8N_3O_3F$: Theoretical: C, 53.02; H, 3.24; N, 16.86; Found: C, 53.27; H, 3.02; N, 16.69.

EXAMPLE 12

4-Carboxy-1-(2,3-dichlorophenyl)-5-pyrazolecarboxamide.

A 15 g. portion of ethyl 1-(2,3-dichlorophenyl)-5-cyano-4-pyrazolecarboxylate was stirred under reflux overnight in 200 ml. of ethanol with 6 g. of potassium hydroxide. The reaction mixture was chromatographed over silica gel, and the product-containing fractions were combined and evaporated to dryness. The residues were recrystallized from ethanol-water to obtain 1.31 g. of the desired product, m.p. 228°–230°, which was identified by elemental analysis.

Calculated for: $C_{11}H_7N_3O_3Cl_2$: Theoretical: C, 44.03; H, 2.35; N, 14.00; Found: C, 44.04; H, 2.39; N, 13.88.

EXAMPLE 13

4-Carboxy-1-(3-chloro-4-methylphenyl)-5-pyrazolecarboxamide.

A 9.5 g. portion of ethyl 1-(3-chloro-4-methylphenyl)-5-cyano-4-pyrazolecarboxylate was dissolved in 250 ml. of ethanol, and 2 g. of potassium hydroxide was added. The mixture was then stirred under reflux for 30 minutes. One hundred ml. of water was added, and the mixture was stirred under reflux for an additional 4 hours. Isolation of the product was attempted, but it was found to be a difficultly separable mixture, and the entire reaction mixture was returned to the flask, redissolved in aqueous ethanol and refluxed for 1 hour on the steam bath with 6 g. of additional potassium hydroxide. The mixture was then diluted with aqueous acetic acid and filtered, and the solids were dried and identified as 5.2 g. of the desired product, m.p. 228°–232° dec. It was identified by elemental analysis.

Calculated for: $C_{12}H_{10}N_3O_3Cl$: Theoretical: C, 51.53; H, 3.60; N, 15.02; Found: C, 51.80; H, 3.36; N, 14.92.

EXAMPLE 14

Methyl 5-aminocarbonyl-1-(3-chlorophenyl)-4-pyrazolecarboxylate.

A 2.2 g. portion of 4-carboxy-1-(3-chlorophenyl)-5-pyrazolecarboxamide was suspended in 40 ml. of methanol, and hydrogen chloride was bubbled through the mixture for about 1 minute. The mixture was then stirred under reflux for 2 hours, poured into ice-water, and made basic with dilute aqueous sodium hydroxide. The mixture was filtered, and the solids were dried and crystallized from toluene to obtain 1.7 g. of the desired product, m.p. 191°–192°. The elemental analysis was as follows.

Calculated for: $C_{12}H_{10}N_3O_3Cl$: Theoretical: C, 51.53; H, 3.60; N, 15.02; Found: C, 51.23; H, 3.71; N, 14.83.

EXAMPLE 15

Allyl 5-aminocarbonyl-1-(3-chlorophenyl)-4-pyrazolecarboxylate.

A 3.33 g. portion of 4-carboxy-1-(3-chlorophenyl)-5-pyrazolecarboxamide was slurried in 35 ml. of methanol, and 0.68 g. of sodium methoxide was added. The methanol was removed under vacuum to leave the sodium salt of the starting compound. That salt was combined with 1.26 g. of triethylamine and 1.51 g. of allyl bromide in 35 ml. of toluene, and the mixture was stirred under reflux overnight. The mixture was then poured into 150 ml. of ice-water, made basic with saturated sodium bicarbonate solution and extracted with 150 ml. of ethyl acetate. The organic layer was washed with brine, dried and evaporated under vacuum to obtain a solid, which was recrystallized from toluene to obtain 1.48 g. of purified product, m.p. 132°–133°. Its elemental analysis was as follows.

Calculated for: $C_{14}H_{12}N_3O_3Cl$: Theoretical: C, 55.00; H, 3.96; N, 13.74; Found: C, 55.15; H, 3.96; N, 13.70.

EXAMPLE 16

Ethyl 5-aminocarbonyl-1-(3-chlorophenyl)-4-pyrazolecarboxylate.

A 2.5 g. portion of 4-carboxy-1-(3-chlorophenyl)-5-pyrazolecarboxamide was suspended in 50 ml. of absolute ethanol, made acid, and esterified and isolated as described in Example 14 above. The product was 1.64 g. of the desired product, m.p. 132°, and its elemental analysis was as follows.

Calculated for: $C_{13}H_{12}N_3O_3Cl$: Theoretical: C, 53.16; H, 4.12; N, 14.31; Found: C, 53.37; H, 4.04; N, 14.61.

EXAMPLE 17

Methyl 5-aminocarbonyl-1-(3-methylphenyl)-4-pyrazolecarboxylate.

Hydrogen chloride gas was bubbled for 1 minute into a suspension of 3 g. of 4-carboxy-1-(3-methylphenyl)-5-pyrazolecarboxamide in 30 ml. of methanol. The mixture was then stirred under reflux for 2 hours and was cooled overnight. It was then poured into 150 ml. of ice and water and made basic with dilute sodium hydroxide. The precipitate was recovered by filtration, dried and recrystallized from toluene, treating with charcoal, to obtain 1.16 g of the desired product, m.p. 167°–168°. It analysis was as follows.

Calculated for: $C_{13}H_{13}N_3O_3$: Theoretical: C, 60.23; H, 5.05; N, 16.21; Found: C, 60.18; H, 4.99; n, 16.08.

EXAMPLE 18

4-Carboxy-1-(3-methylphenyl)-5-pyrazolecarboxamide, sodium salt.

Three g. of 4-carboxy-1-(3-methylphenyl)-5-pyrazolecarboxamide was slurried in 30 ml. of methanol, and 0.66 g. of sodium methoxide was added. The mixture was stirred briefly, and was filtered and evaporated to dryness. The residue was dissolved in methanol, treated with charcoal, and recrystallized. The product was very hygroscopic and was dried for 8 hours at 100° before analysis.

Calculated for: $C_{12}H_{10}N_3O_3Na$: Theoretical: C, 53.94; H, 3.77; N, 15.72; Found: C, 54.11; H, 3.73; N, 15.52.

EXAMPLE 19

4-Carboxy-1-(3-chlorophenyl)-5-pyrazolecarboxamide, sodium salt.

A 6.14 g. portion of 4-carboxy-1-(3-chlorophenyl)-5-pyrazolecarboxamide was slurried in 60 ml. of methanol, and 1.25 g. of sodium methoxide was added. The mixture was stirred for a few minutes, and was then filtered. The filtrate was evaporated to dryness under vacuum, and the residue was dissolved in 50 ml. of methanol and crystallized by the addition of diethyl ether. The solids were collected by filtration and identified after drying as 4.55 g. of the desired salt, m.p. 274°-276°. Its elemental analysis was as follows.

Calculated for: $C_{11}H_7N_3O_3ClNa$: Theoretical: C, 45.93; H, 2.45; N, 14.61; Found: C, 46.10; H, 2.26; N, 14.58.

EXAMPLE 20

4-Carboxy-1-(3-chlorophenyl)-5-pyrazolecarboxamide, potassium salt.

A 4.25 g. portion of 4-carboxy-1-(3-chlorophenyl)-5-pyrazolecarboxamide was slurried in 40 ml. of absolute ethanol with 1.03 g. of 85% potassium hydroxide, and the mixture was heated to the reflux temperature. A little water was added to the refluxing mixture to obtain complete solution, and it was then allowed to cool to ambient temperature. Finally, it was chilled in the refrigerator and filtered to obtain 3.32 g. of the desired product, m.p. above 300° dec. The elemental analysis, calculated for $C_{11}H_7N_3O_3ClK$, was as follows.

Theoretical: C, 43.50; H, 2.32; N, 13.83; Found: C, 43.26; H, 2.09; N, 13.55.

EXAMPLE 21

4-Carboxy-1-(3-chlorophenyl)-5-pyrazolecarboxamide, isopropylamine salt.

A 4.25 g. portion of 4-carboxy-1-(3-chlorophenyl)-5-pyrazolecarboxamide and 1.42 g. of isopropylamine were added to 50 ml. of absolute ethanol and stirred for a few minutes. The mixture was then evaporated to dryness and recrystallized from methanol-diethyl ether to obtain 4.4 g. of the desired product, m.p. 157°-164°. The elemental analysis, calculated for $C_{14}H_{14}N_4O_3Cl$, was as follows.

Theoretical: C, 52.10; H, 4.68; N, 17.36; Found: C, 52.16; H, 4.77; N, 17.19.

EXAMPLE 22

4-Carboxy-1-(3-chlorophenyl)-5-pyrazolecarboxamide, tetrabutylammonium salt.

A 3.26 g. portion of 4-carboxy-1-(3-chlorophenyl)-5-pyrazolecarboxamide was slurried in 50 ml. of methanol and 12 ml. of 1M tetrabutyl ammonium hydroxide solution was added. The mixture was stirred for 30 minutes, and evaporated to dryness under vacuum to obtain 5.2 g. of product, m.p. 120°-121°. The product was identified by elemental analysis.

Calculated for: $C_{27}H_{43}N_4O_3Cl$: Theoretical: N, 11.05; Found: N, 11.07.

EXAMPLE 23

1 4-Carboxy-1-(3,4-dimethylphenyl)-5-pyrazolecarboxamide.

A 2.5 g. portion of ethyl 5-cyano-1-(3,4-dimethylphenyl)-4-pyrazolecarboxylate was hydrolysed in 50 ml. of ethanol and 12 ml. of water with 1.3 g. of potassium hydroxide under reflux for 2¼ hours. The mixture was then cooled and poured into 300 ml. of water. The aqueous mixture was filtered, made acid with concentrated hydrochloric acid, and filtered. The solids were dried and recrystallized from ethanol/water to obtain 1.62 g. of the desired product, m.p. 231°-232.5°. Its elemental analysis was as follows:

Calculated for: $C_{13}H_{13}N_3O_3$. Theoretical: C, 60.23; H, 5.05; N, 16.21; Found: C, 60.47; H, 4.94; N, 16.05.

PREPARATION 1

Ethyl 5-chloro-1-(3-methylphenyl)-4-pyrazolecarboxylate.

A 38.5 g. portion of 3-methylphenylhydrazine hydrochloride and 52.4 g. of diethyl ethoxymethylenemalonate were slurried in 250 ml. of ethanol, and to the mixture was added 46 g. of 50% aqueous sodium hydroxide and 250 ml. of water. The temperature was controlled at 37° with an ice bath. The mixture was then stirred overnight at ambient temperature, and the ethanol was removed under vacuum. The resulting suspension was cooled and the salt was removed by filtration. The solids were washed with two 200 ml. portions of dichloromethane, and were then heated to 50° in 1 liter of water. The mixture was made acid to pH 1 with hydrochloric acid, and was stirred overnight at ambient temperature. The solids were filtered out and dried to obtain 57.4 g. of ethyl 5-hydroxy-1-(3-methylphenyl)-4-pyrazolecarboxylate, m.p. 85°-86.5°.

A 54.4 g. portion of the product was added to 100 ml. of butanol and 200 ml. of concentrated hydrochloric acid, and the mixture was heated to reflux. Heating was continued until the disappearance of the carboxylate was indicated by thin layer chromatography. The butanol was then removed under vacuum to obtain 43.4 g. of 5-hydroxy-1-(3-methylphenyl)pyrazole hydrochloride, m.p. 136°-20 140°.

A 40.4 g. portion of phosphorus oxychloride was cooled to 10° under nitrogen, and to it was slowly added 8.9 g. of dimethylformamide. The mixture was stirred for 30 minutes at ambient temperature, and to it was added in small portions 21.4 g. of the above intermediate. The mixture was then heated to 50° for a time, and then was held for 18 hours at 100°. Fifty ml. of ethanol was added to the cooled mixture, and it was then poured into 500 ml. of ice-water. The aqueous mixture was extracted three times with 250 ml. portions of ethyl acetate, and the combined organic layers were washed with brine, dried and evaporated to obtain 23.5 g. of oil. The oil was dissolved in toluene and crystallized by addition of petroleum ether to obtain 16.5 g. of 5-chloro-1-(3-methylphenyl)-4-pyrazolecarboxaldehyde, m.p. 54°-57°.

Five and four-tenths g. of 50% hydrogen peroxide was added dropwise to 17.2 g. of concentrated sulfuric acid at 15°, and the mixture was stirred at ambient temperature for 2 hours. It was added dropwise to a 5° solution of 4.4 g. of the above intermediate pyrazole in 41.4 ml. of ethanol, while the temperature was held below 15°. After the addition, the mixture was cooled to 5° and stirred for 30 minutes. It was then allowed to warm slowly to ambient temperature overnight, and was then diluted with 50 ml. of water. It was extracted with ethyl acetate, and the organic layer was dried and evaporated under vacuum to obtain 4.6 g. of ethyl 5-chloro-1-(3-methylphenyl)-4-pyrazolecarboxylate.

EXAMPLE 24

4-Carboxy-1-(3-ethylphenyl)-5-pyrazolcarboxamide.

A 60.6 g. portion of 3-ethylaniline was added to 132 g. of concentrated hydrochloric acid and 67 g. of ice at 0°, and an additional 67 g. of ice was added and the was cooled to 0°again. To it was added 36.3 g. of sodium nitrite dissolved in 75 ml. of water, dropwise over a period of 1 hour while the temperature was held below 6°. At the same time, a solution of potassium sulfite was prepared by bubbling sulfur dioxide through a solution of 163.8 g. of potassium hydroxide in 750 ml. of water. The sulfur dioxide addition was continued to a pH of 4.7. Then 67 g. of ice was added and the solution was cooled to 0°.

The two preparations were mixed together as rapidly as possible, while the temperature increased to 8°. The mixture was then heated on a steam bath to 70° and stirred at that temperature for 1 hour. It was then cooled to 0°, and the precipitate was separated by filtration and dried. The solids were recrystallized from a large amount of ethanol to obtain 70.9 g. of potassium 3-ethylphenylhydrazine sulfonate, m.p. dec. greater than 195°.

A 15.0 g. portion of the above intermediate was stirred in 150 ml. of water and 75 ml. of hydrochloric acid with a small amount of charcoal at 80°, and the mixture was filtered while hot. The filtrate was cooled to ambient temperature overnight, and precipitation began immediately upon swirling the solution. The solids were separated by filtration and dried to obtain 5.5 g. of 3-ethylphenylhydrazine hydrochloride, m.p. 147°-157°.

A 10.7 g. portion of the above intermediate, obtained from successive reactions, was combined with 10.5 g. of ethyl (ethoxymethylene)cyanoacetate and 10.2 g. of sodium acetate in 100 ml. of ethanol, and the mixture was stirred under reflux for about 20 hours. The mixture was then poured slowly into 400 ml. of ice-water with good agitation, and the solids were separated by filtration and dried. The solids were recrystallized from aqueous ethanol to obtain 12.7 g. of ethyl 5-amino-1-(3-ethylphenyl)-4-pyrazolecarboxylate, m.p. 79°-79.5°.

A 10.2 g. portion of the above intermediate was dissolved in the minimum amount of chloroform, and hydrogen chloride gas was bubbled through the solution for 1 minute at ambient temperature. Then nitrosyl chloride gas was bubbled through it for 20 minutes while the temperature was held in the range 20°-35° with an ice bath. The mixture was then heated on a steam bath to drive off excess nitrosyl chloride, and it was dried through phase separation paper and the organic portion was evaporated under vacuum. The residue was purified by high performance liquid chromatography, eluting with 1,2-dichloroethane. The product-containing fractions were combined and evaporated under vacuum to obtain 2.9 g. of ethyl 5-chloro-1-(3-ethylphenyl)-4-pyrazolecarboxylate, an oil.

An 8.9 g. portion of the above intermediate, obtained by successive reactions, was combined with 35 ml. of dimethylformamide and 3.4 g. of sodium cyanide, and the mixture was heated for 6 hours at about 100°. It was then cooled, a small amount of additional sodium cyanide was added, and the mixture was heated at 100° for 2 hours more. It was then cooled, and poured into 300 ml. of ice-water. The mixture was extracted with 300 ml. of diethyl ether, and the organic layer was dried and evaporated to obtain 7.9 g. of oily product which was purified by high performance liquid chromatography, eluting with 1,2-dichloroethane. Evaporation of the product-containing fractions gave 6.1 g. of ethyl 5-cyano-1-(3-ethylphenyl)-4-pyrazolecarboxylate, an oil.

A 2.5 g. portion of the above intermediate was added to 25 ml. of ethanol containing 1.6 g. of potassium hydroxide, and the mixture was heated at the reflux temperature for 20 minutes. Five ml. of water was added, the mixture was heated under reflux for 1.5 hours, and it was then poured into 100 ml. of water. The mixture was made acid with concentrated hydrochloric acid, and was chilled overnight and filtered to obtain 2.0 g. of the desired product, m.p. 176°-177.5°. Its elemental analysis was as follows.

Calculated for: $C_{13}H_{13}N_3O_3$: Theoretical: C, 60.23; H, 5.05; N, 16.21; Found: C, 60.03; H, 4.83; N, 15.93.

EXAMPLE 25

4-Carboxy-1-(3-methoxyphenyl)-5-pyrazolecarboxamide.

A 34.9 g. portion of 3-methoxyphenylhydrazine hydrochloride was added to 300 ml. of acetic acid, 100 ml. of water, 36 g. of sodium acetate and 37.2 g. of ethyl (ethoxymethylene)cyanoacetate. The mixture was heated overnight on a steam bath, and was then cooled and poured into 1 liter of ice-water with vigorous agitation. The mixture was filtered, and the solids were air-dried and recrystallized from aqueous ethanol with charcoal to obtain 27.4 g. of ethyl 5-amino-1-(3-methoxyphenyl)-4-pyrazolecarboxylate, m.p. 66°-67°.

A 13.3 g. portion of the above intermediate was dissolved in 80 ml. of bromoform and the mixture was cooled to 5°. To it was added 10.5 g. of t-butyl nitrite, dropwise, and the mixture was then allowed to warm to ambient temperature and was heated on a steam bath for 15 minutes. It was then evaporated under vacuum to obtain 21.1 g. of dark oil, which was dissolved in ethyl acetate. The solution was washed with 1N hydrochloric acid, with water, with saturated sodium bicarbonate, and with brine, and was then dried and evaporated under vacuum to obtain a dark oil, which was purified by high performance liquid chromatography, eluting with 1:3 ethyl acetate:hexane, to obtain 10.6 g. of ethyl 5-bromo-1-(3-methoxyphenyl)-4-pyrazolecarboxylate, m.p. 77°-79°.

A 3.6 g. portion of the above intermediate was combined with 1.2 g. of sodium cyanide in 20 ml. of dimethylformamide, and the mixture was heated for 10 hours at 100°. An additional 0.3 g. of sodium cyanide was added, and the mixture was heated overnight at 100° and was poured into 100 ml. of ice-water. The precipitate was separated by filtration and dried, and was recrystallized from ethanol with charcoal to obtain 1.0 g. of ethyl 5-cyano-1-(3-methoxyphenyl)-4-pyrazolecarboxylate, m.p. 84°-85°.

An 0.95 g. portion of the above intermediate was added to 25 ml. of ethanol and 0.6 g. of potassium hydroxide, and the mixture was heated to reflux. Ten ml. of water was added, and the mixture was heated under reflux for 1.5 hours. It was then cooled and filtered, and the filtrate was poured into 100 ml. of water. The aqueous mixture was made acid with concentrated hydrochloric acid, and was vigorously stirred and then chilled overnight. The precipitate was separated by filtration and dried, and was then recrystallized from aqueous ethanol to obtain 0.4 g. of the desired product, m.p. 213°–216°. Its elemental analysis was as follows.

Calculated for: $C_{12}H_{11}N_3O_4$: Theoretical: C, 55.17; H, 4.24; N, 16.08; Found C, 55.12; H, 3.99; N, 15.83.

The compounds of the present invention have been carefully tested to demonstrate their activity in inhibiting the formation of pollen. Some of the tests reported below were carried out before it was learned that the compounds must be supplied before anther formation. It is now believed that the compounds were applied too late in some tests and therefore could not be effective. However, since it is now impossible to know which tests were so applied, all questionable tests will be reported here.

Test 1

The experiment recorded here was a field experiment carried out in central Indiana, U.S.A. The experiment was started by planting strips of Auburn and Beau wheat in the autumn. Some strips were planted on October 4, and others on October 14. The field was fertilized at the time of planting with a combination of fertilizers appropriate for the growth of wheat. Adjacent the strips of Auburn and Beau wheat were planted pollen-shedding plots of mixed Caldwell, Auburn and Titan wheat in the ratio 1:1:2. The pollen-shedding plots were planted on October 1 at the rate of 100 lb. of seed per acre.

The test compound in this experiment was that of Example 1 above. The compound was formulated for application in 1:1 by volume acetone:denatured alcohol. The organic solution was diluted in water, containing 0.25% of polysorbate 20 for application. All applications were at the volume rate of 500 gallons per acre, and were applied as a foliar spray to the test plots.

The first application of compound was made on April 26 following the planting of the wheat. Where multiple applications of compound were made, the later applications were at intervals of one week.

The test plots were laid out in the bands of Auburn and Beau wheat, which became the female plots for production of hybrid wheat, pollinated by the pollen-shedding plots of wheat. Each test plot was 4 rows × 13 ft. in size.

At the time of wheat head emergence, some heads in each treated plot were bagged with small-grain pollinator glassine bags. Five heads in each row of each test plot were bagged.

When the seed was formed, the number of seeds per head in the bagged plants provided a measure of the extent to which pollen formation was inhibited, because those seed could have been formed only by self-pollination. The number of seeds per head in unbagged plants in each test plot was also counted, as was the number of seeds per head in untreated control plots.

Two plots were treated according to each treatment regime and the results are averaged in the table below.

The data are reported separately below for each variety of wheat and each planting date. The earlier-planted plots are described as "age 1", and the later as "age 2". The columns headed "fertility" report the number of seeds per head of the treated bagged plants, as percentage of untreated controls, and therefore give a direct measurement of pollen formation. The columns headed "hybrid" report the difference between the number of seeds per head of treated unbagged plants and seeds per head of treated bagged plants, as percentage of untreated controls. Thus, that column reports the amount of hybrid seed produced, compared to the seed produced by untreated control plants. The purity of the hybrid seed produced may be estimated by comparing the "fertility" percentage with the "hybrid" percentage.

TABLE 1

| | | Age 1 | | | | Age 2 | | | |
|---|---|---|---|---|---|---|---|---|---|
| | | Auburn | | Beau | | Auburn | | Beau | |
| Rate | Appl'ns | Fertility | Hybrid | Fertility | Hybrid | Fertility | Hybrid | Fertility | Hybrid |
| 1 lb/A | 1 | 90% | 12% | 73% | 26% | 100% | 0% | 98% | 5% |
| 1 | 2 | 39 | 41 | 65 | 13 | 52 | 45 | 83 | 10 |
| 1 | 3 | 4 | 73 | 23 | 51 | 4 | 71 | 44 | 40 |
| 3 | 1 | 12 | 79 | 20 | 58 | 51 | 34 | 35 | 50 |
| 3 | 2 | 0 | 92 | 7 | 63 | 0 | 78 | 24 | 63 |
| 3 | 3 | 0 | 57 | 0 | 49 | 1 | 75 | 0 | 74 |
| 5 | 1 | 20 | 58 | 27 | 46 | 2 | 79 | 37 | 45 |
| 5 | 2 | 0 | 40 | 0 | 22 | 0 | 56 | 4 | 56 |
| 5 | 3 | 0 | 33 | 1 | 47 | 0 | 55 | 0 | 59 |
| 10 | 1 | 0 | 70 | 0 | 55 | 0 | 73 | 1 | 78 |
| 10 | 2 | 0 | 33 | 0 | 32 | 0 | 59 | 0 | 49 |
| 10 | 3 | 0 | 3 | 0 | 6 | 0 | 8 | 0 | 41 |
| 15 | 1 | 0 | 27 | 0 | 29 | 0 | 44 | 0 | 54 |
| 15 | 2 | 0 | 19 | 0 | 35 | 0 | 54 | 0 | 44 |
| 15 | 3 | 0 | 4 | 1 | 1 | 0 | 16 | 0 | 16 |

Additional plots in the same block of Auburn and Beau wheat plots were treated once, on either May 4 or May 10, following planting of the wheat in October. The results of these experiments are shown in the table below.

TABLE 2

| Rate | Appl'ns | Age 1 | | | | Age 2 | | | |
|---|---|---|---|---|---|---|---|---|---|
| | | Auburn | | Beau | | Auburn | | Beau | |
| | | Fertility | Hybrid | Fertility | Hybrid | Fertility | Hybrid | Fertility | Hybrid |
| 1 lb/A | May 4 | 95 | 2 | 86 | 6 | 104 | 8 | 99 | 2 |
| 3 | May 4 | 30 | 57 | 48 | 31 | 20 | 73 | 74 | 18 |
| 5 | May 4 | 9 | 62 | 28 | 45 | 37 | 49 | 34 | 38 |
| 10 | May 4 | 5 | 72 | 32 | 39 | 14 | 68 | 15 | 50 |
| 15 | May 4 | 0 | 53 | 6 | 53 | 0 | 55 | 14 | 53 |
| 1 | May 10 | 67 | 22 | 85 | 0 | 29 | 65 | 77 | 9 |
| 3 | May 10 | 17 | 60 | 63 | 6 | 14 | 76 | 59 | 35 |
| 5 | May 10 | 12 | 58 | 54 | 18 | 13 | 82 | 35 | 40 |
| 10 | May 10 | 0 | 67 | 23 | 37 | 0 | 86 | 3 | 79 |
| 15 | May 10 | 0 | 26 | 2 | 30 | 3 | 56 | 0 | 49 |

Test 2

The compound of Example 1 was applied to 61 varieties of wheat. Each test plot consisted of three 2-ft. hand-planted rows, with 2-ft. spaces between the groups of three. The plots were planted in central Indiana on October 5. On the following May 5, two of the three replicates were sprayed with the compound of Example 1 at 5 lb. per acre and 10 lb. per acre, and the third replicate provided an untreated control.

Plants were bagged, and the seed set of bagged, unbagged and untreated plants were counted as described in Test 1. Pollen for these experiments was provided by bands of the same pollen-shedding mixture of wheat described in Test 1.

The data from this group of experiments are reported below in summary form, as the number of the wheat varieties which exhibited fertility of the bagged treated plants in various ranges, compared to the fertility of untreated control plants.

TABLE 3

| Fertility | 5 lbs./Acre | 10 lbs./Acre |
|---|---|---|
| <10% | 6 | 16 |
| 10–29% | 4 | 9 |
| 30–49% | 10 | 14 |
| 50–69% | 10 | 9 |
| 70–89% | 14 | 6 |
| more than 89% | 16 | 7 |

Test 3

A standardized greenhouse test was used to evaluate the compounds of the present invention. The test was begun by planting Waldron wheat in 4 inch pots, 4 seeds per pot, in a sterilized sand/loam soil. The wheat was allowed to grow in a favorable greenhouse environment, and the plants were treated 3 times with a test compound. The first application was about 22 days after the seed was planted, and the second and third applications were about 3 and about 10 days after the first.

Each compound was formulated for testing by dissolving the proper amount for two replicates and three applications, depending on the concentration to be tested, in 5 ml. of 1:1 by volume acetone:denatured alcohol, containing 10% by volume of polysorbate 20. Compounds which did not dissolve were finely dispersed in the solvent. The organic mixture was then diluted to 30 ml. with deionized water at about ambient temperature, and the aqueous dispersion was evenly sprayed over the foliage of two pots of wheat.

Untreated control plants were provided in each experiment.

The results of experiments are reported below as the number of spikelets produced by the treated plants, and the number of seed per spikelet. The average number of spikelets per normal plant is about 15, and the number of seed per spikelet varies in the range of about 1.5 to 2.5.

In the tables below, the results of replicate experiments have been averaged. When the results of an experiment were not different from the results of the contemporaneous untreated controls, the inactivity is indicated merely by "N".

TABLE 4

| 1500 ppm concentration | | |
|---|---|---|
| Compound of Example No. | Spikelets | Seed/Spikelet |
| 1 | 15.2 | 0.17 |
| 1 | 15.7 | 0.28 |
| 1 | 13.0 | 0 |
| 2 | N | |
| 3 | 14.6 | 0.35 |
| 4 | 15.7 | 0.11 |
| 5 | 13.3 | 0 |
| 6 | 14.6 | 0.13 |
| 7 | 14.2 | 0.40 |
| 8 | 15.7 | 0.64 |
| 9 | 16.0 | 0.44 |
| 10 | 14.7 | 0.24 |
| 11 | 16.0 | 0.73 |
| 14 | 15.0 | 0.67 |
| 15 | 16.1 | 0.53 |
| 16 | 14.8 | 0.47 |
| 19 | 14.8 | 0.19 |
| 20 | 15.2 | 0.33 |
| 21 | 15.1 | 0.12 |

TABLE 5

| 1200 ppm concentration | | |
|---|---|---|
| Compound of Example No. | Spikelets | Seed/Spikelet |
| 1 | 10.6 | 0 |
| 1 | 11.7 | 0.22 |
| 2 | N | |
| 5 | 13.5 | 0.01 |

TABLE 6

| 1000 ppm concentration | | |
|---|---|---|
| Compound of Example No. | Spikelets | Seed/Spikelet |
| 1 | 9.0 | 0 |
| 1 | 9.4 | 0 |
| 1 | 12.0 | 0.16 |
| 1 | 11.2 | 0.27 |
| 1 | N | |
| 1 | N | |
| 1 | N | |
| 1 | 12.9 | 0 |
| 1 | 13.8 | 0 |
| 1 | 13.5 | 0.50 |
| 1 | 12.3 | 0.41 |

TABLE 6-continued

1000 ppm concentration

| Compound of Example No. | Spikelets | Seed/Spikelet |
|---|---|---|
| 1 | 13.6 | 0.68 |
| 1 | 13.7 | 0.84 |
| 1 | 15.3 | 1.28 |
| 1 | 12.7 | 0.89 |
| 1 | 15.5 | 0.81 |
| 1 | 15.6 | 0.69 |
| 1 | 14.0 | 0.15 |
| 1 | 15.3 | 0.08 |
| 1 | 15.0 | 0.98 |
| 1 | 14.3 | 1.10 |
| 1 | 16.0 | 0.48 |
| 1 | 16.7 | 0.32 |
| 1 | 15.8 | 0.38 |
| 1 | 15.8 | 0.34 |
| 1 | 16.7 | 0.54 |
| 1 | 16.7 | 0.32 |
| 1 | 15.7 | 1.92 |
| 1 | 15.5 | 0.68 |
| 1 | 14.7 | 0.26 |
| 1 | 15.8 | 1.22 |
| 2 | 9.2 | 0.12 |
| 2 | N | |
| 3 | 10.9 | 0.14 |
| 3 | N | |
| 4 | N | |
| 5 | 13.2 | 0.13 |
| 5 | 12.9 | 0.23 |
| 6 | N | |
| 7 | N | |
| 7 | 15.4 | 0.57 |
| 8 | 12.0 | 0 |
| 8 | 12.5 | 0.63 |
| 9 | N | |
| 9 | 14.3 | 1.68 |
| 10 | 15.0 | 0.95 |
| 14 | 11.7 | 0.06 |
| 14 | 10.5 | 0.65 |
| 14 | 14.0 | 0.70 |
| 15 | N | |
| 16 | 12.3 | 0.45 |
| 16 | 14.8 | 1.60 |
| 16 | 15.5 | 0.93 |
| 19 | 13.5 | 0.25 |
| 19 | 15.7 | 0.09 |
| 20 | 17.0 | 0.32 |
| 20 | 14.3 | 0.07 |
| 21 | 14.0 | 0.25 |
| 21 | 16.0 | 1.30 |

TABLE 7

800 ppm concentration

| Compound of Example No. | Spikelets | Seed/Spikelet |
|---|---|---|
| 1 | 9.8 | 0.05 |
| 1 | 12.8 | 0.04 |
| 1 | 12.0 | 0.26 |
| 1 | N | |
| 1 | N | |
| 1 | 11.5 | 0.75 |
| 1 | 14.0 | 1.02 |
| 1 | 14.3 | 1.27 |
| 1 | 15.3 | 1.01 |
| 1 | 14.0 | 0.42 |
| 1 | 14.7 | 0.19 |
| 1 | 15.5 | 0.92 |
| 1 | 14.3 | 0.68 |
| 1 | 15.7 | 1.67 |
| 1 | 16.0 | 1.02 |
| 1 | 14.0 | 0.07 |
| 1 | 15.9 | 0.79 |
| 5 | 13.0 | 0.09 |
| 7 | 14.2 | 0.80 |
| 8 | 14.0 | 0.42 |
| 9 | 16.0 | 1.92 |
| 10 | 15.7 | 1.06 |
| 14 | 12.0 | 0.31 |

TABLE 7-continued

800 ppm concentration

| Compound of Example No. | Spikelets | Seed/Spikelet |
|---|---|---|
| 14 | 15.5 | 1.47 |
| 16 | 14.8 | 1.26 |
| 19 | 13.3 | 0.23 |
| 20 | 15.0 | 0.07 |
| 21 | 15.0 | 0.95 |

TABLE 8

600 ppm concentration

| Compound of Example No. | Spikelets | Seed/Spikelet |
|---|---|---|
| 1 | 9.0 | 0.39 |
| 1 | 11.2 | 0.64 |
| 1 | N | |
| 1 | N | |
| 1 | N | |
| 1 | 12.3 | 1.01 |
| 1 | 14.5 | 1.93 |
| 1 | 13.7 | 1.88 |
| 1 | 14.8 | 0.99 |
| 1 | 13.8 | 0.42 |
| 1 | 14.0 | 0.27 |
| 1 | 14.8 | 0.62 |
| 1 | 14.8 | 1.48 |
| 1 | 14.5 | 1.65 |
| 1 | 15.8 | 1.25 |
| 1 | 14.7 | 0.50 |
| 1 | 16.0 | 0.67 |
| 2 | N | |
| 3 | N | |
| 5 | 13.3 | 0.33 |
| 5 | N | |
| 7 | N | |
| 7 | 15.6 | 0.77 |
| 8 | 13.3 | 0.36 |
| 8 | 14.0 | 0.49 |
| 9 | 15.0 | 1.87 |
| 10 | 15.3 | 1.90 |
| 14 | N | |
| 14 | 15.8 | 0.94 |
| 16 | 14.8 | 1.09 |
| 16 | 15.5 | 0.93 |
| 19 | 14.5 | 0.32 |
| 20 | 16.0 | 0.53 |
| 21 | 15.3 | 0.94 |

TABLE 9

400 ppm concentration

| Compound of Example No. | Spikelets | Seed/Spikelet |
|---|---|---|
| 1 | N | |
| 1 | N | |
| 1 | 11.7 | 1.61 |
| 1 | 12.7 | 1.18 |
| 1 | 14.0 | 1.55 |
| 1 | 14.0 | 1.54 |
| 1 | 16.5 | 0.69 |
| 1 | 14.3 | 0.65 |
| 1 | 14.8 | 0.15 |
| 1 | 15.0 | 1.03 |
| 1 | 15.0 | 1.31 |
| 1 | N | |
| 1 | N | |
| 1 | 14.3 | 0.44 |
| 1 | N | |
| 7 | 15.2 | 1.72 |
| 8 | 13.3 | 1.55 |
| 9 | N | |
| 10 | N | |
| 14 | N | |
| 14 | N | |
| 16 | N | |
| 19 | 14.5 | 0.37 |
| 20 | 15.3 | 0.63 |

TABLE 9-continued

| Compound of Example No. | 400 ppm concentration | |
|---|---|---|
| | Spikelets | Seed/Spikelet |
| 21 | 16.0 | 1.81 |

TABLE 10

| Compound of Example No. | 300 ppm concentration | |
|---|---|---|
| | Spikelets | Seed/Spikelet |
| 1 | 8.5 | 0.26 |
| 3 | N | |
| 5 | N | |
| 7 | N | |

TABLE 11

| Compound of Example No. | 200 ppm concentration | |
|---|---|---|
| | Spikelets | Seed/Spikelet |
| 1 | N | |
| 1 | N | |
| 1 | 13.0 | 1.10 |
| 1 | 13.5 | 1.65 |
| 1 | 13.8 | 1.66 |
| 1 | 14.3 | 1.86 |
| 1 | 14.3 | 1.29 |
| 1 | 14.0 | 0.56 |
| 1 | 14.3 | 1.42 |
| 1 | 14.0 | 1.88 |
| 1 | N | |
| 1 | N | |
| 1 | 15.0 | 1.08 |
| 1 | N | |
| 7 | N | |
| 8 | 13.8 | 1.71 |
| 9 | N | |
| 10 | N | |
| 14 | N | |
| 14 | N | |
| 16 | N | |
| 19 | 15.3 | 0.12 |
| 20 | 16.0 | 1.21 |
| 21 | 14.3 | 2.01 |

TABLE 12

| Compound of Example No. | 100 ppm concentration | |
|---|---|---|
| | Spikelets | Seed/Spikelet |
| 1 | 9.5 | 1.21 |
| 1 | N | |
| 1 | 11.7 | 1.79 |
| 1 | 10.9 | 1.79 |
| 1 | 13.5 | 1.78 |
| 1 | 14.5 | 1.97 |
| 1 | 14.0 | 1.77 |
| 1 | 14.5 | 0.66 |
| 1 | 14.3 | 1.60 |
| 1 | 14.3 | 1.92 |
| 1 | N | |
| 1 | N | |
| 3 | N | |
| 5 | N | |
| 7 | N | |
| 7 | N | |
| 8 | N | |
| 8 | 13.0 | 1.81 |
| 9 | N | |
| 10 | N | |
| 14 | N | |
| 14 | N | |
| 16 | N | |
| 19 | 15.0 | 1.47 |
| 20 | 15.5 | 1.36 |

TABLE 12-continued

| Compound of Example No. | 100 ppm concentration | |
|---|---|---|
| | Spikelets | Seed/Spikelet |
| 21 | 14.7 | 1.97 |

Test 4

This test was carried out substantially according to the method described in Test 3 above, except that the compounds were applied only twice, at an interval of 4 days. In other respects, the test method and the method of reporting data were the same.

TABLE 13

| Compound of Example No. | Concentration ppm. | Spikelets | Seed/Spikelet |
|---|---|---|---|
| 1 | 1000 | 13.4 | 0 |
| 1 | 1000 | 13.7 | 0.58 |
| 1 | 800 | 11.2 | 0 |
| 1 | 800 | 14.2 | 1.05 |
| 1 | 800 | 10.0 | 0 |
| 1 | 600 | 13.6 | 0 |
| 1 | 600 | 11.0 | 0.91 |
| 1 | 600 | N | |
| 1 | 600 | 9.0 | 0.02 |
| 1 | 300 | 13.3 | 0.07 |
| 1 | 300 | N | |
| 1 | 100 | N | |
| 1 | 100 | N | |

Test 5

The test method of Test 4 was applied again, but in this case the interval between the two applications of compound was 6 days.

TABLE 14

| Compound of Example No. | Concentration ppm. | Spikelets | Seed/Spikelet |
|---|---|---|---|
| 1 | 1500 | 12.2 | 0.57 |
| 1 | 1000 | N | |
| 1 | 1000 | 14.5 | 0.03 |
| 1 | 1000 | N | |
| 1 | 1000 | 14.2 | 1.04 |
| 1 | 1000 | N | |
| 1 | 1000 | 10.7 | 0.06 |
| 1 | 1000 | 12.3 | 0.89 |
| 1 | 1000 | 13.0 | 0.23 |
| 1 | 800 | 15.2 | 0.80 |
| 1 | 800 | 11.7 | 0.07 |
| 1 | 800 | N | |
| 1 | 800 | N | |
| 1 | 800 | N | |
| 1 | 800 | N | |
| 1 | 800 | N | |
| 1 | 800 | 12.7 | 0.18 |
| 1 | 600 | 13.3 | 0.03 |
| 1 | 600 | 15.3 | 1.41 |
| 1 | 600 | 13.0 | 0.81 |
| 1 | 600 | N | |
| 1 | 600 | N | |
| 1 | 600 | N | |
| 1 | 600 | N | |
| 1 | 600 | 10.8 | 0.26 |
| 1 | 600 | 12.5 | 0.06 |
| 1 | 400 | N | |
| 1 | 400 | 13.3 | 0.80 |
| 1 | 400 | 11.8 | 0.17 |
| 1 | 400 | N | |
| 1 | 400 | N | |
| 1 | 400 | N | |
| 1 | 400 | N | |
| 1 | 400 | 11.7 | 0.31 |
| 1 | 300 | N | |
| 1 | 200 | N | |

TABLE 14-continued

| Compound of Example No. | Concentration ppm. | Spikelets | Seed/ Spikelet |
|---|---|---|---|
| 1 | 200 | 12.0 | 0.50 |
| 1 | 200 | N | |
| 1 | 200 | N | |
| 1 | 200 | N | |
| 1 | 200 | N | |
| 1 | 200 | N | |
| 1 | 100 | N | |
| 1 | 100 | N | |
| 1 | 100 | N | |
| 1 | 100 | N | |
| 1 | 100 | N | |
| 1 | 100 | N | |
| 1 | 100 | N | |
| 1 | 100 | N | |
| 10 | 1500 | 12.7 | 0.01 |
| 10 | 1000 | 12.3 | 0.03 |
| 10 | 1000 | 12.6 | 0.03 |
| 10 | 1000 | 12.8 | 0.08 |
| 10 | 1000 | 14.2 | 0 |
| 10 | 1000 | N | |
| 10 | 1000 | 12.0 | 0.46 |
| 10 | 1000 | 13.0 | 0.85 |
| 10 | 1000 | 12.0 | 0.25 |
| 10 | 800 | N | |
| 10 | 800 | N | |
| 10 | 800 | 12.0 | 0.89 |
| 10 | 800 | 13.0 | 0.69 |
| 10 | 800 | 13.7 | 0.42 |
| 10 | 800 | 13.8 | 0.12 |
| 10 | 800 | 12.9 | 0.05 |
| 10 | 800 | 13.8 | 0 |
| 10 | 600 | 11.7 | 0 |
| 10 | 600 | 14.5 | 0.09 |
| 10 | 600 | 13.7 | 0.18 |
| 10 | 600 | 14.2 | 0.18 |
| 10 | 600 | 11.0 | 0.73 |
| 10 | 600 | 13.0 | 0.81 |
| 10 | 600 | N | |
| 10 | 600 | 12.0 | 0.63 |
| 10 | 400 | 10.7 | 0.94 |
| 10 | 400 | 12.0 | 0.67 |
| 10 | 400 | N | |
| 10 | 400 | N | |
| 10 | 400 | 12.0 | 0.18 |
| 10 | 400 | 15.5 | 0.03 |
| 10 | 400 | 13.3 | 0.30 |
| 10 | 300 | 13.2 | 0.14 |
| 10 | 200 | 13.6 | 0.28 |
| 10 | 200 | 14.0 | 0.20 |
| 10 | 200 | 14.2 | 0.01 |
| 10 | 200 | N | |
| 10 | 200 | N | |
| 10 | 200 | N | |
| 10 | 200 | N | |
| 10 | 100 | N | |
| 10 | 100 | N | |
| 10 | 100 | N | |
| 10 | 100 | N | |
| 10 | 100 | 16.7 | 0.54 |
| 10 | 100 | 12.2 | 0.30 |
| 10 | 100 | 12.3 | 1.10 |
| 10 | 100 | 12.4 | 1.58 |
| 11 | 1000 | N | |
| 11 | 800 | N | |
| 11 | 600 | N | |
| 11 | 400 | N | |
| 11 | 200 | N | |
| 11 | 100 | N | |
| 12 | 1500 | 16.0 | 0.50 |
| 12 | 1000 | N | |
| 12 | 800 | N | |
| 12 | 600 | N | |
| 12 | 400 | N | |
| 12 | 200 | N | |
| 13 | 1500 | 14.7 | 0.20 |
| 13 | 1500 | 14.8 | 0.41 |
| 13 | 1000 | 12.0 | 0.42 |
| 13 | 1000 | 11.6 | 0.56 |
| 13 | 800 | 14.7 | 0.45 |
| 13 | 800 | 12.7 | 0.27 |
| 13 | 600 | N | |
| 13 | 600 | N | |
| 13 | 400 | N | |
| 13 | 300 | N | |
| 13 | 200 | N | |
| 13 | 100 | N | |
| 23 | 1500 | 14.7 | 0.05 |
| 23 | 1500 | 12.8 | 0.07 |
| 23 | 1000 | 13.2 | 0.10 |
| 23 | 1000 | N | |
| 23 | 800 | 12.8 | 0.16 |
| 23 | 600 | N | |
| 23 | 600 | 13.8 | 0.26 |
| 23 | 300 | N | |
| 23 | 300 | 13.2 | 0.24 |
| 23 | 100 | N | |
| 23 | 100 | N | |
| 24 | 1000 | 12.0 | 0 |
| 24 | 600 | 13.0 | 0 |
| 24 | 400 | 11.7 | 0 |
| 24 | 200 | 12.8 | 0.12 |
| 24 | 100 | 12.0 | 0.81 |
| 25 | 400 | 13.1 | 0.04 |
| 25 | 300 | 14.1 | 0.12 |
| 25 | 200 | 14.0 | 0.19 |
| 25 | 100 | 15.6 | 1.18 |
| 25 | 50 | N | |
| 25 | 25 | N | |

Test 6

The experiments reported here were carried out as described above in Test 5, except that the test compound was applied only once, about 21 days after the seed was planted. The data are reported below in the same manner used to report the above tests.

TABLE 15

| Compound of Example No. | Concentration ppm. | Spikelets | Seed/ Spikelet |
|---|---|---|---|
| 1 | 1000 | 13.7 | 0 |
| 1 | 1000 | 13.0 | 1.20 |
| 1 | 800 | 12.5 | 0 |
| 1 | 800 | 11.3 | 0.66 |
| 1 | 600 | 15.0 | 0.06 |
| 1 | 600 | N | |
| 1 | 300 | 14.2 | 0.42 |
| 1 | 300 | N | |
| 1 | 100 | 12.5 | 0.17 |
| 1 | 100 | N | |

Test 7

In these tests, the compounds were applied to the soil in which the wheat plants were growing, rather than to the foliage of the plants. Wheat was grown in the greenhouse as described in Test 3, and compounds were formulated for testing as described in that test, except that the compounds were diluted to a volume of 50 ml. per pot. A single application of compound was made, 20 or 21 days after the wheat was planted. The results of the test were as follows.

TABLE 16

| Compound of Example No. | Concentration ppm. | Spikelets | Seed/ Spikelet |
|---|---|---|---|
| 1 | 1000 | N | |
| 1 | 800 | 10.3 | 0 |
| 1 | 600 | N | |
| 1 | 300 | 11.0 | 0.60 |

Test 8

In the tests reported here, the compounds were formulated and applied as described in Test 3 above, except that small amounts of additional surfactants were added to the aqueous dispersions in an attempt to obtain higher absorption of the compounds by the foliage. Compounds were applied 3 times as described in Test 3, and the results were as follows.

TABLE 17

| Compound of Example No. | Concentration ppm. | Spikelets | Seed/Spikelet |
|---|---|---|---|
| *1% polysorbate 20* | | | |
| 1 | 1000 | 14.8 | 1.23 |
| 1 | 800 | 15.3 | 0.60 |
| 1 | 600 | 15.0 | 1.19 |
| 1 | 400 | 15.2 | 1.47 |
| 1 | 200 | 14.7 | 1.17 |
| 1 | 100 | 15.3 | 1.24 |
| *0.4% Tergitol TMN-6* | | | |
| 1 | 1000 | 16.8 | 0.72 |
| 1 | 800 | 15.0 | 1.10 |
| 1 | 600 | N | |
| 1 | 400 | N | |
| 1 | 200 | N | |
| 1 | 100 | N | |
| *1% Tergitol TMN-6* | | | |
| 1 | 1000 | Herbicidal | |
| 1 | 800 | Herbicidal | |
| 1 | 600 | 13.5 | 1.14 |
| 1 | 400 | 12.3 | 1.26 |
| 1 | 200 | 13.3 | 1.44 |
| 1 | 100 | 12.8 | 1.26 |
| *1% Ortho X-77* | | | |
| 1 | 1000 | 14.5 | 1.58 |
| 1 | 800 | 15.0 | 1.82 |
| 1 | 600 | 14.8 | 1.82 |
| 1 | 400 | 13.0 | 1.48 |
| 1 | 200 | 14.0 | 2.02 |
| 1 | 100 | 14.0 | 1.83 |
| *5 ppm Intensify\** | | | |
| 1 | 1000 | 15.5 | 0.81 |
| 1 | 800 | 14.5 | 0.95 |
| 1 | 600 | 14.3 | 0.79 |
| 1 | 400 | 14.0 | 1.37 |
| 1 | 200 | 14.3 | 1.59 |
| 1 | 100 | 14.0 | 1.89 |
| *20 ppm Intensify* | | | |
| 1 | 1000 | 13.8 | 2.17 |
| 1 | 800 | 12.7 | 1.99 |
| 1 | 600 | 13.0 | 1.67 |
| 1 | 400 | 14.3 | 2.14 |
| 1 | 200 | 13.3 | 2.16 |
| 1 | 100 | 14.5 | 2.24 |
| *40 ppm Intensify* | | | |
| 1 | 1000 | 14.5 | 1.31 |
| 1 | 800 | 14.0 | 2.18 |
| 1 | 600 | 14.5 | 1.47 |
| 1 | 400 | 14.0 | 1.96 |
| 1 | 200 | 13.5 | 2.03 |
| 1 | 100 | 13.8 | 2.30 |

*49% aqueous NH$_4$SCN and Al(OH)$_3$

Test 9

In these tests, the compounds were formulated in various ways in order to assess the formulation effect on performance. In all these tests, wheat was grown in the greenhouse as described in Test 3, and compounds were applied 3 times to the foliage of the plants as described in that test. The formulations used are described briefly at the heading of the data in the table below.

TABLE 18

| Compound of Example No. | Concentration ppm. | Spikelets | Seed/Spikelet |
|---|---|---|---|
| *5 ml. dimethylsulfoxide, 5 ml. acetone/ethanol/polysorbate 20, 20 ml. water* | | | |
| 1 | 300 | N | |
| 1 | 200 | N | |
| 1 | 100 | N | |
| 1 | 50 | N | |
| 1 | 25 | N | |
| *suspension of powdered compound in water* | | | |
| 1 | 1000 | 15.8 | 1.41 |
| 1 | 800 | 15.0 | 1.08 |
| 1 | 600 | 17.2 | 0.81 |
| 1 | 400 | N | |
| 1 | 200 | N | |
| 1 | 100 | N | |
| *suspension of powdered compound in water plus 1% soybean oil* | | | |
| 1 | 1000 | 17.0 | 0.98 |
| 1 | 800 | 15.0 | 1.61 |
| 1 | 600 | 15.0 | 0.73 |
| 1 | 400 | N | |
| 1 | 200 | N | |
| 1 | 100 | N | |
| *dimethylformamide solution dispersed in water* | | | |
| 1 | 1000 | 14.7 | 1.82 |
| 1 | 1000 | 14.5 | 2.16 |
| 1 | 1000 | 15.0 | 0.45 |
| 1 | 1000 | 14.7 | 0.52 |
| 1 | 1000 | 15.7 | 0.17 |
| 1 | 1000 | 14.7 | 0.15 |
| 1 | 800 | 14.7 | 2.00 |
| 1 | 800 | 14.7 | 2.04 |
| 1 | 800 | 13.8 | 0.45 |
| 1 | 800 | 14.8 | 0 |
| 1 | 800 | 16.2 | 0.80 |
| 1 | 800 | 15.5 | 0.92 |
| 1 | 600 | 14.2 | 1.97 |
| 1 | 600 | 14.7 | 2.09 |
| 1 | 600 | 14.0 | 0.37 |
| 1 | 600 | 14.0 | 0.13 |
| 1 | 600 | 14.5 | 0.91 |
| 1 | 600 | 14.8 | 0.56 |
| 1 | 400 | 14.7 | 1.80 |
| 1 | 400 | 13.2 | 1.89 |
| 1 | 400 | 14.3 | 1.01 |
| 1 | 400 | 14.5 | 1.27 |
| 1 | 400 | 14.8 | 0.57 |
| 1 | 400 | 15.0 | 1.30 |
| 1 | 200 | 14.3 | 1.72 |
| 1 | 200 | 14.8 | 1.98 |
| 1 | 200 | 14.0 | 2.05 |
| 1 | 200 | 14.0 | 1.59 |
| 1 | 200 | 13.7 | 1.95 |
| 1 | 200 | 14.3 | 2.00 |
| 1 | 100 | 14.7 | 1.73 |
| 1 | 100 | 13.8 | 2.04 |
| 1 | 100 | 13.5 | 1.74 |
| 1 | 100 | 14.0 | 1.98 |
| 1 | 100 | 12.5 | 1.78 |
| 1 | 100 | 14.7 | 1.96 |

Test 10

The experiments reported here were carried out substantially like those of Test 8, except that the compounds were applied only twice, at a 4-day interval. The compounds were formulated for foliar application as described in Test 3 above, except that the acetone/ethanol solution of the compound was diluted with 2 ml. of dimethylsulfoxide before being diluted to 30 ml. with water.

TABLE 19

| Compound of Example No. | Concentration ppm. | Spikelets | Seed/Spikelet |
|---|---|---|---|
| 1 | 1000 | 13.3 | 0 |

TABLE 19-continued

| Compound of Example No. | Concentration ppm. | Spikelets | Seed/ Spikelet |
|---|---|---|---|
| 1 | 1000 | 13.5 | 0.74 |
| 1 | 800 | 9.5 | 0 |
| 1 | 800 | N | |
| 1 | 600 | 12.7 | 0.05 |
| 1 | 600 | N | |
| 1 | 300 | 12.0 | 0.26 |
| 1 | 300 | N | |
| 1 | 100 | N | |
| 1 | 100 | N | |

Test 11

In these experiments, the compounds were applied only once, when the wheat plants were 36 days old. The wheat plants were reared as described in Test 3, and the compounds were formulated and applied as described in Test 3, except that 1 ml. of dimethylsulfoxide was added to the acetone/ethanol solution before it was diluted to 30 ml. with water.

TABLE 20

| Compound of Example No. | Concentration ppm. | Spikelets | Seed/ Spikelet |
|---|---|---|---|
| 1 | 1000 | 10.7 | 0.88 |
| 1 | 1000 | 13.3 | 0 |
| 1 | 800 | N | |
| 1 | 800 | 11.2 | 0.04 |
| 1 | 600 | N | |
| 1 | 600 | 12.8 | 0 |
| 1 | 300 | N | |
| 1 | 300 | 12.8 | 0.61 |
| 1 | 100 | N | |
| 1 | 100 | 14.3 | 0 |

Test 12

In these tests, a preferred compound of the invention, that of Example 1, was applied on successive days to pots of wheat which had all been planted at the same time, in order to determine the optimum time for application of the compound. The formulation of the compound and application to the wheat was carried out as described in Test 3 above, except that the compound was applied only once to each pot, on the day after planting indicated in the tables below.

TABLE 21

| Compound of Example 1, 1000 ppm. Concentration | | |
|---|---|---|
| Day After Planting | Spikelets | Seed/ Spikelet |
| 15 | N | |
| 16 | N | |
| 17 | N | |
| 18 | N | |
| 19 | N | |
| 20 | N | |
| 21 | N | |
| 22 | N | |
| 23 | N | |
| 24 | 16.5 | 0.80 |
| 25 | N | |
| 26 | N | |

TABLE 22

| Compound of Example 1, 1500 ppm. Concentration | | |
|---|---|---|
| Day After Planting | Spikelets | Seed/ Spikelet |
| 18 | N | |
| 19 | N | |

TABLE 22-continued

| Compound of Example 1, 1500 ppm. Concentration | | |
|---|---|---|
| Day After Planting | Spikelets | Seed/ Spikelet |
| 20 | N | |
| 21 | N | |
| 22 | N | |
| 23 | 11.7 | 0.69 |
| 24 | 11.7 | 1.22 |
| 25 | 10.4 | 0.40 |
| 26 | 14.7 | 0.27 |
| 27 | 11.6 | 0.78 |
| 28 | 13.6 | 0.20 |
| 29 | 13.4 | 0.10 |
| 30 | 15.1 | 0.89 |
| 31 | 15.9 | 0.20 |
| 32 | 15.4 | 0.09 |
| 33 | 15.9 | 0.05 |
| 34 | 15.9 | 0.04 |
| 35 | 15.9 | 0.28 |
| 36 | 15.6 | 0.14 |
| 37 | 15.6 | 0.70 |
| 38 | 15.6 | 0.33 |
| 39 | N | |
| 40 | N | |
| 41 | 15.6 | 0.75 |

Test 13

A single compound was applied on successive days to pots of wheat which had been planted at the same time, substantially as described in the test above, except that in this test, the compound was applied to the surface of the soil, rather than to the foliage. In each instance, 50 ml. of an aqueous dispersion containing 1000 ppm of the compound of Example 1 was applied. The compound was formulated by dissolving it in 10 ml. of the acetone/ethanol/polysorbate 20 solution described in Test 3 above, and diluting that solution to 50 ml. with water. Two replicate pots of wheat were used on each day. The results were as follows:

TABLE 23

| Day After Planting | Spikelets | Seed/ Spikelet |
|---|---|---|
| 17 | 9.4 | 0 |
| 18 | Herbicidal | |
| 19 | 8.5 | 0 |
| 20 | Herbicidal | |
| 21 | 9.8 | 0.01 |
| 22 | Herbicidal | |
| 23 | 10.0 | 0 |
| 24 | 9.5 | 0 |
| 25 | 9.2 | 0 |
| 26 | 11.4 | 0 |
| 27 | 10.5 | 0 |
| 28 | 10.1 | 0 |
| 29 | 12.2 | 0 |
| 30 | 12.0 | 0 |
| 31 | 10.8 | 0 |
| 32 | 11.2 | 0 |
| 33 | 9.5 | 0 |
| 34 | 9.8 | 0.18 |
| 35 | 12.2 | 0 |
| 36 | 12.5 | 0.03 |
| 37 | 10.2 | 0.01 |
| 38 | 10.0 | 0.91 |
| 39 | 11.0 | 0.36 |

Test 14

The compound of Example 10 was used in a test where Waldron wheat seedlings were sprayed with a 500 ppm. concentration of the compound, formulated substantially as described in Test 3 above. A large number of pots of wheat seeds were planted on Nov. 16 in the greenhouse, and two pots were treated on each day thereafter. All of the pots were observed on Feb. 20, in order to identify the range of age wherein the wheat plants were sensitive to the treatment.

No activity was obtained from treatments of plants less than 27 days old (when the first node of the plants had moved up three centimeters, and the head was 2 mm. long), and no activity was obtained from treatments of plants older than 42 days (when the head was 3 cm. long).

The following table reports the results observed from plants which were treated when they were in the range of 27 to 42 days old.

TABLE 24

| Day After Planting | Spikelets | Seed/Spikelet |
|---|---|---|
| 27 | N | |
| 27 | 14.0 | 0.36 |
| 28 | 13.0 | 0.73 |
| 28 | N | |
| 29 | 13.0 | 0.50 |
| 29 | N | |
| 30 | 13.0 | 0.35 |
| 30 | 12.0 | 0.17 |
| 31 | 13.0 | 0.04 |
| 31 | 12.0 | 0.08 |
| 32 | 12.7 | 0.47 |
| 32 | 12.0 | 0.33 |
| 33 | 13.0 | 0.04 |
| 33 | 10.7 | 0 |
| 34 | 11.3 | 0.41 |
| 34 | 12.7 | 0.5 |
| 35 | 12.7 | 0 |
| 35 | 13.0 | 0 |
| 36 | 15.0 | 0 |
| 36 | 14.7 | 0 |
| 37 | 14.0 | 0 |
| 37 | 11.0 | 0 |
| 38 | 13.0 | 0 |
| 38 | 15.0 | 0 |
| 39 | 13.3 | 0 |
| 39 | N | |
| 40 | 13.3 | 0 |
| 40 | 15.0 | 0 |
| 41 | 13.0 | 0.62 |
| 41 | 12.7 | 0.32 |
| 42 | 11.0 | 0.59 |
| 42 | 12.7 | 0.16 |

Test 15

The compound of Example 1 was applied to Waldron wheat seed before it was planted in pots as described in Test 3 above. The amounts of compound ranged from 1% to 5% of the weight of the seed. The wheat was raised in the greenhouse, and the effect of the seed treatment was observed and reported below. Eight pots of wheat were planted with each batch of treated seed, and each pot was observed and reported separately.

TABLE 25

| % of Compound | Spikelets | Seed/Spikelet |
|---|---|---|
| 1 | N | |
| 1 | N | |
| 1 | N | |
| 1 | N | |
| 1 | N | |
| 1 | N | |
| 1 | N | |
| 1 | N | |
| 2 | N | |
| 2 | N | |

TABLE 25-continued

| % of Compound | Spikelets | Seed/Spikelet |
|---|---|---|
| 2 | N | |
| 2 | N | |
| 2 | N | |
| 2 | N | |
| 2 | N | |
| 3 | N | |
| 3 | Herbicidal | |
| 3 | N | |
| 3 | N | |
| 3 | N | |
| 3 | N | |
| 3 | N | |
| 3 | N | |
| 4 | N | |
| 4 | N | |
| 4 | N | |
| 4 | N | |
| 4 | N | |
| 4 | N | |
| 4 | N | |
| 4 | 10.7 | 0.41 |
| 4 | N | |
| 5 | N | |
| 5 | N | |
| 5 | Herbicidal | |
| 5 | 11.3 | 0 |
| 5 | 10.7 | 0.25 |
| 5 | 10.0 | 0.20 |
| 5 | N | |
| 5 | N | |

Test 16

The compound of Example 1 was tested on Larker barley, in a greenhouse test which was carried out in a manner substantially similar to Test 3 above. A single barley plant was grown in each 10-inch pot in sterilized soil in the greenhouse, and the compound was applied 5 times to each pot. The applications were made over a period of 3 weeks, and the amounts of aqueous dispersions were increased from 10 ml., at the first application, to 15, 20 and finally 30 ml. at the last application, in order to wet the increasing area of the foliage.

The untreated control plants produced 2.50 seeds per spikelet, on the average. The plants treated with 600 ppm. of compound 1 produced, on average, 0.81 seeds per spikelet, and the plants treated with 1000 ppm. of compound 1 produced 0.62 seeds per spikelet.

Additional pots of barley were treated with soil drench applications of compound 1 at the same times that the foliar applications described above were made. Each soil drench treatment consisted of 100 ml. of aqueous dispersion containing 1000 ppm. of compound. The plant treated in that manner produced no seeds.

Test 17

The compound of Example 1 was tested in the greenhouse on Waldron wheat by drenching the soil with 50 ml. of dispersion per 4" pot. Five ml. of acetone/ethanol/polysorbate 20 solution, containing the proper amount of the compound, was dispersed in 45 ml. of water to prepare the dispersions described in the table below. Four replicate 4" pots of four seeds each were treated with each treatment rate, at different dates as shown below.

TABLE 26

| Day After Planting | Concentration ppm. | Spikelets | Seed/Spikelet |
|---|---|---|---|
| 0 | 1000 | 12.4 | 0.01 |
| 0 | 800 | 15.3 | 0.04 |

TABLE 26-continued

| Day After Planting | Concentration ppm. | Spikelets | Seed/ Spikelet |
|---|---|---|---|
| 0 | 600 | 15.3 | 0.20 |
| 0 | 400 | 15.1 | 0.18 |
| 0 | 200 | 14.1 | 0.57 |
| 0 | 100 | 13.5 | 1.01 |
| 7 | 1000 | 14.1 | 0 |
| 7 | 800 | 13.6 | 0.02 |
| 7 | 600 | 14.1 | 0.04 |
| 7 | 400 | 13.5 | 0.05 |
| 7 | 200 | 13.5 | 0.55 |
| 7 | 100 | 13.3 | 0.87 |
| 14 | 1000 | 12.8 | 0.01 |
| 14 | 800 | 12.5 | 0.01 |
| 14 | 600 | 12.8 | 0 |
| 14 | 400 | 13.8 | 0 |
| 14 | 200 | 13.3 | 0.05 |
| 14 | 100 | 12.8 | 0.66 |
| 21 | 1000 | 13.0 | 0 |
| 21 | 800 | 12.3 | 0 |
| 21 | 600 | 12.2 | 0 |
| 21 | 400 | 12.7 | 0 |
| 21 | 200 | 13.7 | 0.03 |
| 21 | 100 | 13.0 | 0.08 |

Test 18

Compounds were tested in the greenhouse on Waldron wheat by incorporating the compounds in the soil. The proper amount of each compound, named in the table below, was dissolved in 1.5 ml. of acetone/ethanol/polysorbate 20 solution, and that solution was diluted with water to 10 ml. The aqueous dispersion was divided into 3 aliquots, and each was sprayed into the soil to be used to plant one 4" pot, with good mixing of the soil. Wheat seeds were planted in the soil the same day the soil was treated, and the fertility of the plants was measured and reported in the same manner used before.

TABLE 27

| Compound of Example No. | Rate, mg./pot | Spikelets | Seed/ Spikelet |
|---|---|---|---|
| 1 | 1 | 12.5 | 0.45 |
| 1 | 3 | 12.4 | 0.02 |
| 1 | 6 | 11.8 | 0.01 |
| 1 | 11 | 13.3 | 0 |
| 1 | 11 | 12.6 | 0.03 |
| 1 | 22 | 12.4 | 0.03 |
| 1 | 45 | 13.3 | 0.02 |
| 8 | 1 | N | |
| 8 | 3 | N | |
| 8 | 6 | 11.1 | 1.13 |
| 8 | 11 | 12.9 | 0.56 |
| 8 | 11 | 11.9 | 0.65 |
| 8 | 22 | 11.7 | 0.35 |
| 8 | 45 | 11.8 | 0.50 |
| 10 | 0.5 | N | |
| 10 | 0.5 | Herbicidal | |
| 10 | 0.5 | Herbicidal | |
| 10 | 1 | 12.0 | 0.58 |
| 10 | 1 | 12.0 | 0 |
| 10 | 1 | 12.0 | 0.04 |
| 10 | 1 | 12.1 | 0.07 |
| 10 | 3 | 11.8 | 0 |
| 10 | 5 | 9.3 | 0.04 |
| 10 | 5 | 12.0 | 0 |
| 10 | 5 | 12.0 | 0 |
| 10 | 6 | 11.5 | 0 |
| 10 | 10 | 12.0 | 0 |
| 10 | 10 | 10.0 | 0 |
| 10 | 10 | 10.0 | 0 |
| 10 | 11 | 11.8 | 0 |
| 14 | 1 | 12.5 | 0.17 |
| 14 | 3 | 12.0 | 0 |
| 14 | 6 | 11.4 | 0 |
| 14 | 11 | 11.9 | 0 |

TABLE 27-continued

| Compound of Example No. | Rate, mg./pot | Spikelets | Seed/ Spikelet |
|---|---|---|---|
| 14 | 11 | 11.3 | 0.04 |
| 14 | 22 | 12.6 | 0 |
| 14 | 45 | 12.0 | 0 |
| 19 | 1 | 11.0 | 0.16 |
| 19 | 3 | 11.3 | 0.06 |
| 19 | 6 | 12.7 | 0 |
| 19 | 11 | 11.7 | 0 |
| 19 | 11 | 11.8 | 0 |
| 19 | 22 | 11.8 | 0 |
| 19 | 45 | 12.2 | 0.03 |
| 23 | 0.5 | N | |
| 23 | 0.5 | Herbicidal | |
| 23 | 0.5 | N | |
| 23 | 1 | N | |
| 23 | 1 | N | |
| 23 | 1 | N | |
| 23 | 5 | 14.0 | 0 |
| 23 | 5 | 10.7 | 0.03 |
| 23 | 5 | Herbicidal | |
| 23 | 10 | 11.5 | 0 |
| 23 | 10 | 9.3 | 0.04 |
| 23 | 10 | 12.0 | 0 |

Test 19

Compounds of the present invention were applied to Waldron wheat seed as seed treatments and tested in the greenhouse. The amount of the compound in each test is shown in the table below as a percent by weight of the seed. The compounds were ground to a fine powder and dusted over the seed in a tumbler; a thin film of glue was applied to the seed before adding the powdered compound. The results were as follows; each result is the mean of 4 replicate pots.

TABLE 28

| Compound of Example No. | Rate | Spikelets | Seed/ Spikelet |
|---|---|---|---|
| 1 | 0.5% | 6.8 | 1.52 |
| 1 | 1 | 5.5 | 1.72 |
| 1 | 2 | 6.0 | 0.85 |
| 1 | 4 | 3.5 | 1.43 |
| 1 | 6 | N | |
| 1 | 8 | N | |
| 19 | 2 | N | |
| 19 | 4 | 3.2 | 1.73 |
| 19 | 6 | 1.5 | 1.00 |
| 19 | 8 | 3.5 | 0.86 |

Test 20

Field tests were carried out substantially as described in Test 1 above. Here, both the test plots and the pollen-shedding strips were Caldwell wheat, and were planted on Oct. 4. The compounds were formulated as described in Test 1. The volume rate was 475 gallons per acre, except as otherwise noted below, and all applications were as a foliar spray directly over the rows.

Applications were made on 3 days in the spring. The applications were quite late because the spring was cold and wet and the wheat developed late. The first day was May 9, when the heads of the wheat were still at ground level, and were 5–10 mm. long. The second day was May 15, when the heads were 6–12 mm. long and were about 10 cm. above ground level, and the third date was May 21, when the heads were 2.5–5 cm. long and were in the green anther stage. The third application date was therefore too late.

Five different treatment regimes were used, as
A. Applied once on May 9

B. Applied once on May 15
C. Applied once on May 21
D. Applied twice on May 9 and 15
E. Applied three times.

The application rate which is stated in the tables below is the amount applied per application.

The test plots were 6 rows wide and 13 feet long. Ten heads in each plot were bagged and were counted, as were ten unbagged heads.

The data were collected and reported below as described in Test 1.

TABLE 29

| Compound of Example No. | Rate, lb./A. | Regime | Fertility | Hybrid |
|---|---|---|---|---|
| 1 | 1 | A | 89% | 6% |
| 1 | 1 | B | 94 | 4 |
| 1 | 1 | C | 94 | 0 |
| 1 | 1 | D | 64 | 24 |
| 1 | 1 | E | 40 | 34 |
| 1 | 3 | A | 86 | 0 |
| 1 | 3 | B | 30 | 34 |
| 1 | 3 | C | 83 | 18 |
| 1 | 3 | D | 1 | 69 |
| 1 | 3 | E | 0 | 59 |
| 1 | 5 | A | 5 | 49 |
| 1 | 5 | B | 5 | 45 |
| 1 | 5 | C | 52 | 27 |
| 1 | 5 | D | 0 | 39 |
| 1 | 5 | E | 0 | 33 |
| 1 | 10 | A | 0 | 52 |
| 1 | 10 | B | 1 | 46 |
| 1 | 10 | C | 28 | 23 |
| 1 | 10 | D | 1 | 10 |
| 1 | 10 | E | 0 | 12 |
| 1 | 15 | A | 0 | 32 |
| 1 | 15 | B | 0 | 7 |
| 1 | 15 | C | 15 | 24 |
| 1 | 15 | D | 0 | 0 |
| 1 | 15 | E | 0 | 0 |
| 8 | 3 | A | 76 | 17 |
| 8 | 3 | B | 86 | 11 |
| 8 | 3 | C | 99 | 0 |
| 8 | 3 | D | 93 | 4 |
| 8 | 3 | E | 73 | 17 |
| 8 | 10 | A | 83 | 14 |
| 8 | 10 | B | 74 | 4 |
| 8 | 10 | C | 79 | 9 |
| 8 | 10 | D | 32 | 27 |
| 8 | 10 | E | 12 | 36 |
| 10 | 1 | A | 77 | 17 |
| 10 | 1 | B | 46 | 36 |
| 10 | 1 | C | 86 | 7 |
| 10 | 1 | D | 2 | 60 |
| 10 | 1 | E | 1 | 49 |
| 10 | 3 | A | 8 | 44 |
| 10 | 3 | B | 0 | 58 |
| 10 | 3 | C | 29 | 16 |
| 10 | 3 | D | 0 | 38 |
| 10 | 3 | E | 0 | 25 |
| 10 | 10 | A | 0 | 26 |
| 10 | 10 | B | 0 | 34 |
| 10 | 10 | C | 8 | 17 |
| 10 | 10 | D | 0 | 19 |
| 10 | 10 | E | 0 | 1 |
| 14 | 3 | A | 69 | 20 |
| 14 | 3 | B | 70 | 17 |
| 14 | 3 | C | 86 | 0 |
| 14 | 3 | D | 32 | 22 |
| 14 | 3 | E | 11 | 40 |
| 14 | 10 | A | 3 | 35 |
| 14 | 10 | B | 4 | 36 |
| 14 | 10 | C | 41 | 16 |
| 14 | 10 | D | 0 | 20 |
| 14 | 10 | E | 0 | 5 |
| 19 | 1 | A | 85 | 13 |
| 19 | 1 | B | 86 | 9 |
| 19 | 1 | C | 88 | 10 |
| 19 | 1 | D | 77 | 19 |
| 19 | 1 | E | 50 | 16 |
| 19 | 3 | A | 91 | 10 |
| 19 | 3 | B | 53 | 28 |
| 19 | 3 | C | 96 | 5 |
| 19 | 3 | D | 14 | 47 |
| 19 | 3 | E | 2 | 59 |
| 19 | 10 | A | 0 | 39 |
| 19 | 10 | B | 0 | 50 |
| 19 | 10 | C | 43 | 23 |
| 19 | 10 | D | 0 | 14 |
| 19 | 10 | E | 0 | 23 |

In the following tests, the spray volume was 160 gal./A.; in all other respects the method was as set out above.

TABLE 30

| Compound of Example No. | Rate, lb./A. | Regime | Fertility | Hybrid |
|---|---|---|---|---|
| 1 | 3 | A | 60 | 17 |
| 1 | 3 | B | 20 | 42 |
| 1 | 3 | C | 68 | 16 |
| 1 | 3 | D | 0 | 48 |
| 1 | 3 | E | 0 | 0 |
| 1 | 10 | A | 0 | 56 |
| 1 | 10 | B | 1 | 67 |
| 1 | 10 | C | 68 | 32 |
| 1 | 10 | D | 0 | 9 |
| 1 | 10 | E | 0 | 1 |

In the following test, the spray volume was only 80 gal./A.

TABLE 31

| Compound of Example No. | Rate, lb./A. | Regime | Fertility | Hybrid |
|---|---|---|---|---|
| 1 | 3 | A | 79 | 13 |
| 1 | 3 | B | 3 | 53 |
| 1 | 3 | C | 89 | 7 |
| 1 | 3 | D | 1 | 59 |
| 1 | 3 | E | 0 | 53 |
| 1 | 10 | A | 0 | 90 |
| 1 | 10 | B | 0 | 22 |
| 1 | 10 | C | 0 | 50 |
| 1 | 10 | D | 33 | 29 |
| 1 | 10 | E | 0 | 18 |

Test 21

Tests of Compounds 1 and 10, in the form of granular formulations, were carried out by applying the formulations broadcast over the surface of field plots of Caldwell wheat. The wheat had been planted in early November, and the test formulations were applied in the spring, at the time when the first node of the plants had just begun to ascend. The formulae of the granular formulations are listed below, in the section where formulations are discussed. The proper amount of each of the formulations was applied to the soil to provide the application rate of the active compound which is listed in the various lines in the table below. The results of the tests are reported in the same manner used in the tables just above, as a percentage fertility of treated, bagged plants compared to the yield of hybrid seed.

TABLE 32

| Compound of Example No. | Formulation | Rate, lb./A. | Fertility | Hybrid |
|---|---|---|---|---|
| 1 | 1 | 0.76 | 100% | 0% |
| 1 | 2 | 1.9 | 64 | 16 |
| 1 | 3 | 2.3 | 25 | 42 |
| 1 | 4 | 3.8 | 33 | 34 |

TABLE 32-continued

| Compound of Example No. | Formulation | Rate, lb./A. | Fertility | Hybrid |
|---|---|---|---|---|
| 1 | 5 | 5.7 | 3 | 48 |
| 1 | 6 | 7.6 | 5 | 36 |
| 1 | 7 | 9.5 | 0 | 14 |
| 1 | 8 | 11.4 | 0 | 23 |
| 1 | 9 | 19 | 0 | 2 |
| 1 | 10 | 28.5 | 0 | 0 |
| 10 | 11 | 0.95 | 90 | 2 |
| 10 | 12 | 2.85 | 5 | 52 |
| 10 | 13 | 4.75 | 1 | 32 |
| 10 | 14 | 7.12 | 0 | 17 |

Test 22

Field tests were carried out substantially as described in Test 20 above, except that the volume rate per acre was varied and a number of different formulations were used. Applications were made on three days in the spring to the fall-planted wheat. The spring was quite early and warm, and the first application was made on Apr. 17, when the first node of the plants had just begun to ascend. The second application was made four days thereafter, and the third application, three days after that. The third application was probably made after the anthers of most of the plants had formed, and was therefore too late. Five different treatment regimes were used, as described in Test 20 above. The formulations used are identified by their numbers in the formulation section below. The work "tech" refers to a formulation such as described in Test 3 above.

The data were collected and reported below as described in Test 20.

TABLE 33

Compound of Example 10

| Rate, lb./A. | Volume, gal./A. | Formulation | Regime | Fertility | Hybrid |
|---|---|---|---|---|---|
| 0.5 | 150 | Tech. | A | 100% | 0 |
| 0.5 | 150 | Tech. | B | 36 | 36 |
| 0.5 | 150 | Tech. | C | 95 | 0 |
| 0.5 | 150 | Tech. | D | 6 | 54 |
| 0.5 | 150 | Tech. | E | 2 | 54 |
| 0.5 | 100 | Tech. | A | 92 | 0 |
| 0.5 | 100 | Tech. | B | 100 | 0 |
| 0.5 | 100 | Tech. | C | 93 | 6 |
| 0.5 | 100 | Tech. | D | 25 | 37 |
| 0.5 | 100 | Tech. | E | 8 | 53 |
| 0.5 | 50 | Tech. | A | 89 | 0 |
| 0.5 | 50 | Tech. | B | 88 | 0 |
| 0.5 | 50 | Tech. | C | 82 | 0 |
| 0.5 | 50 | Tech. | D | 34 | 34 |
| 0.5 | 50 | Tech. | E | 3 | 50 |
| 0.5 | 25 | Tech. | A | 85 | 0 |
| 0.5 | 25 | Tech. | B | 82 | 4 |
| 0.5 | 25 | Tech. | C | 82 | 3 |
| 0.5 | 25 | Tech. | D | 67 | 8 |
| 0.5 | 25 | Tech. | E | 58 | 21 |
| 0.75 | 150 | Tech. | A | 94 | 0 |
| 0.75 | 150 | Tech. | B | 26 | 37 |
| 0.75 | 150 | Tech. | C | 70 | 0 |
| 0.75 | 150 | Tech. | D | 23 | 43 |
| 0.75 | 150 | Tech. | E | 7 | 44 |
| 0.75 | 100 | Tech. | A | 98 | 0 |
| 0.75 | 100 | Tech. | B | 72 | 7 |
| 0.75 | 100 | Tech. | C | 80 | 0 |
| 0.75 | 100 | Tech. | D | 52 | 21 |
| 0.75 | 100 | Tech. | E | 3 | 51 |
| 0.75 | 50 | Tech. | A | 79 | 10 |
| 0.75 | 50 | Tech. | B | 71 | 13 |
| 0.75 | 50 | Tech. | C | 79 | 7 |
| 0.75 | 50 | Tech. | D | 10 | 50 |
| 0.75 | 50 | Tech. | E | 5 | 42 |
| 0.75 | 25 | Tech. | A | 98 | 0 |
| 0.75 | 25 | Tech. | B | 94 | 0 |
| 0.75 | 25 | Tech. | C | 80 | 6 |
| 0.75 | 25 | Tech. | D | 33 | 0 |
| 0.75 | 25 | Tech. | E | 30 | 48 |
| 1.0 | 150 | Tech. | A | 73 | 2 |
| 1.0 | 150 | Tech. | B | 73 | 0 |
| 1.0 | 150 | Tech. | C | 53 | 12 |
| 1.0 | 150 | Tech. | D | 10 | 54 |
| 1.0 | 150 | Tech. | E | 2 | 50 |
| 1.0 | 100 | Tech. | A | 59 | 23 |
| 1.0 | 100 | Tech. | B | 75 | 1 |
| 1.0 | 100 | Tech. | C | 63 | 19 |
| 1.0 | 100 | Tech. | D | 5 | 49 |
| 1.0 | 100 | Tech. | E | 2 | 51 |
| 1.0 | 50 | Tech. | A | 35 | 40 |
| 1.0 | 50 | Tech. | B | 55 | 24 |
| 1.0 | 50 | Tech. | C | 34 | 42 |
| 1.0 | 50 | Tech. | D | 11 | 51 |
| 1.0 | 50 | Tech. | E | 4 | 42 |
| 1.0 | 25 | Tech. | A | 79 | 2 |
| 1.0 | 25 | Tech. | B | 92 | 0 |
| 1.0 | 25 | Tech. | C | 58 | 16 |
| 1.0 | 25 | Tech. | D | 33 | 26 |
| 1.0 | 25 | Tech. | E | 23 | 26 |
| 1.5 | 150 | Tech. | A | 51 | 31 |
| 1.5 | 150 | Tech. | B | 84 | 5 |
| 1.5 | 150 | Tech. | C | 18 | 32 |
| 1.5 | 150 | Tech. | D | 4 | 56 |
| 1.5 | 150 | Tech. | E | 3 | 47 |
| 1.5 | 100 | Tech. | A | 22 | 46 |
| 1.5 | 100 | Tech. | B | 41 | 25 |
| 1.5 | 100 | Tech. | C | 30 | 26 |
| 1.5 | 100 | Tech. | D | 4 | 49 |
| 1.5 | 100 | Tech. | E | 4 | 41 |
| 1.5 | 50 | Tech. | A | 31 | 51 |
| 1.5 | 50 | Tech. | B | 60 | 13 |
| 1.5 | 50 | Tech. | C | 27 | 31 |
| 1.5 | 50 | Tech. | D | 17 | 40 |
| 1.5 | 50 | Tech. | E | 3 | 40 |
| 1.5 | 25 | Tech. | A | 80 | 7 |
| 1.5 | 25 | Tech. | B | 93 | 0 |
| 1.5 | 25 | Tech. | C | 85 | 0 |
| 1.5 | 25 | Tech. | D | 37 | 13 |
| 1.5 | 25 | Tech. | E | 2 | 44 |
| 0.5 | 150 | 15 | A | 90 | 0 |
| 0.5 | 150 | 15 | B | 81 | 4 |
| 0.5 | 150 | 15 | C | 88 | 0 |
| 0.5 | 150 | 15 | D | 44 | 30 |
| 0.5 | 150 | 15 | E | 1 | 44 |
| 0.5 | 100 | 15 | A | 90 | 0 |
| 0.5 | 100 | 15 | B | 86 | 0 |
| 0.5 | 100 | 15 | C | 100 | 0 |
| 0.5 | 100 | 15 | D | 63 | 16 |
| 0.5 | 100 | 15 | E | 5 | 58 |
| 0.5 | 50 | 15 | A | 88 | 6 |
| 0.5 | 50 | 15 | B | 100 | 0 |
| 0.5 | 50 | 15 | C | 87 | 5 |
| 0.5 | 50 | 15 | D | 42 | 46 |
| 0.5 | 50 | 15 | E | 24 | 40 |
| 0.5 | 25 | 15 | A | 93 | 0 |
| 0.5 | 25 | 15 | B | 100 | 0 |
| 0.5 | 25 | 15 | C | 98 | 0 |
| 0.5 | 25 | 15 | D | 20 | 57 |
| 0.5 | 25 | 15 | E | 43 | 27 |
| 0.75 | 150 | 15 | A | 79 | 6 |
| 0.75 | 150 | 15 | B | 79 | 2 |
| 0.75 | 150 | 15 | C | 76 | 3 |
| 0.75 | 150 | 15 | D | 16 | 35 |
| 0.75 | 150 | 15 | E | 4 | 36 |
| 0.75 | 100 | 15 | A | 86 | 8 |
| 0.75 | 100 | 15 | B | 66 | 22 |
| 0.75 | 100 | 15 | C | 79 | 10 |
| 0.75 | 100 | 15 | D | 24 | 32 |
| 0.75 | 100 | 15 | E | 4 | 48 |
| 0.75 | 50 | 15 | A | 82 | 1 |
| 0.75 | 50 | 15 | B | 59 | 21 |
| 0.75 | 50 | 15 | C | 84 | 0 |
| 0.75 | 50 | 15 | D | 18 | 55 |
| 0.75 | 50 | 15 | E | 5 | 50 |

TABLE 33-continued

Compound of Example 10

| Rate, lb./A. | Volume, gal./A. | Formulation | Regime | Fertility | Hybrid |
|---|---|---|---|---|---|
| 0.75 | 25 | 15 | A | 90 | 0 |
| 0.75 | 25 | 15 | B | 96 | 0 |
| 0.75 | 25 | 15 | C | 100 | 0 |
| 0.75 | 25 | 15 | D | 50 | 23 |
| 0.75 | 25 | 15 | E | 14 | 60 |
| 1.0 | 150 | 15 | A | 85 | 0 |
| 1.0 | 150 | 15 | B | 69 | 0 |
| 1.0 | 150 | 15 | C | 84 | 1 |
| 1.0 | 150 | 15 | D | 4 | 64 |
| 1.0 | 150 | 15 | E | 3 | 45 |
| 1.0 | 100 | 15 | A | 97 | 0 |
| 1.0 | 100 | 15 | B | 74 | 20 |
| 1.0 | 100 | 15 | C | 48 | 37 |
| 1.0 | 100 | 15 | D | 15 | 52 |
| 1.0 | 100 | 15 | E | 1 | 69 |
| 1.0 | 50 | 15 | A | 84 | 11 |
| 1.0 | 50 | 15 | B | 62 | 32 |
| 1.0 | 50 | 15 | C | 100 | 0 |
| 1.0 | 50 | 15 | D | 15 | 52 |
| 1.0 | 50 | 15 | E | 2 | 44 |
| 1.0 | 25 | 15 | A | 62 | 15 |
| 1.0 | 25 | 15 | B | 80 | 3 |
| 1.0 | 25 | 15 | C | 79 | 3 |
| 1.0 | 25 | 15 | D | 41 | 35 |
| 1.0 | 25 | 15 | E | 9 | 44 |
| 1.5 | 150 | 15 | A | 55 | 14 |
| 1.5 | 150 | 15 | B | 51 | 20 |
| 1.5 | 150 | 15 | C | 8 | 37 |
| 1.5 | 150 | 15 | D | 6 | 38 |
| 1.5 | 150 | 15 | E | 2 | 42 |
| 1.5 | 100 | 15 | A | 41 | 29 |
| 1.5 | 100 | 15 | B | 12 | 43 |
| 1.5 | 100 | 15 | C | 17 | 47 |
| 1.5 | 100 | 15 | D | 1 | 42 |
| 1.5 | 100 | 15 | E | 1 | 36 |
| 1.5 | 50 | 15 | A | 51 | 13 |
| 1.5 | 50 | 15 | B | 32 | 36 |
| 1.5 | 50 | 15 | C | 62 | 16 |
| 1.5 | 50 | 15 | D | 1 | 37 |
| 1.5 | 50 | 15 | E | 1 | 31 |
| 1.5 | 25 | 15 | A | 50 | 5 |
| 1.5 | 25 | 15 | B | 44 | 16 |
| 1.5 | 25 | 15 | C | 58 | 24 |
| 1.5 | 25 | 15 | D | 27 | 22 |
| 1.5 | 25 | 15 | E | 6 | 35 |
| 0.5 | 150 | 16 | A | 88 | 17 |
| 0.5 | 150 | 16 | B | 72 | 14 |
| 0.5 | 150 | 16 | C | 90 | 0 |
| 0.5 | 150 | 16 | D | 22 | 47 |
| 0.5 | 150 | 16 | E | 4 | 52 |
| 0.5 | 100 | 16 | A | 100 | 0 |
| 0.5 | 100 | 16 | B | 94 | 5 |
| 0.5 | 100 | 16 | C | 82 | 4 |
| 0.5 | 100 | 16 | D | 52 | 28 |
| 0.5 | 100 | 16 | E | 16 | 53 |
| 0.5 | 50 | 16 | A | 86 | 7 |
| 0.5 | 50 | 16 | B | 92 | 6 |
| 0.5 | 50 | 16 | C | 95 | 0 |
| 0.5 | 50 | 16 | D | 44 | 45 |
| 0.5 | 50 | 16 | E | 18 | 36 |
| 0.5 | 25 | 16 | A | 90 | 0 |
| 0.5 | 25 | 16 | B | 86 | 3 |
| 0.5 | 25 | 16 | C | 95 | 0 |
| 0.5 | 25 | 16 | D | 68 | 14 |
| 0.5 | 25 | 16 | E | 26 | 50 |
| 0.75 | 150 | 16 | A | 66 | 13 |
| 0.75 | 150 | 16 | B | 66 | 9 |
| 0.75 | 150 | 16 | C | 54 | 27 |
| 0.75 | 150 | 16 | D | 2 | 56 |
| 0.75 | 150 | 16 | E | 2 | 40 |
| 0.75 | 100 | 16 | A | 77 | 0 |
| 0.75 | 100 | 16 | B | 68 | 8 |
| 0.75 | 100 | 16 | C | 58 | 17 |
| 0.75 | 100 | 16 | D | 53 | 16 |
| 0.75 | 100 | 16 | E | 10 | 43 |
| 0.75 | 50 | 16 | A | 77 | 12 |
| 0.75 | 50 | 16 | B | 73 | 7 |
| 0.75 | 50 | 16 | C | 96 | 0 |
| 0.75 | 50 | 16 | D | 31 | 45 |
| 0.75 | 50 | 16 | E | 11 | 40 |
| 0.75 | 25 | 16 | A | 95 | 0 |
| 0.75 | 25 | 16 | B | 90 | 0 |
| 0.75 | 25 | 16 | C | 90 | 0 |
| 0.75 | 25 | 16 | D | 59 | 19 |
| 0.75 | 25 | 16 | E | 7 | 63 |
| 1.0 | 150 | 16 | A | 71 | 17 |
| 1.0 | 150 | 16 | B | 45 | 26 |
| 1.0 | 150 | 16 | C | 43 | 25 |
| 1.0 | 150 | 16 | D | 1 | 64 |
| 1.0 | 150 | 16 | E | 7 | 47 |
| 1.0 | 100 | 16 | A | 64 | 18 |
| 1.0 | 100 | 16 | B | 69 | 8 |
| 1.0 | 100 | 16 | C | 52 | 26 |
| 1.0 | 100 | 16 | D | 12 | 47 |
| 1.0 | 100 | 16 | E | 2 | 53 |
| 1.0 | 50 | 16 | A | 84 | 0 |
| 1.0 | 50 | 16 | B | 61 | 13 |
| 1.0 | 50 | 16 | C | 87 | 0 |
| 1.0 | 50 | 16 | D | 8 | 51 |
| 1.0 | 50 | 16 | E | 2 | 42 |
| 1.0 | 25 | 16 | A | 74 | 8 |
| 1.0 | 25 | 16 | B | 64 | 8 |
| 1.0 | 25 | 16 | C | 72 | 11 |
| 1.0 | 25 | 16 | D | 34 | 30 |
| 1.0 | 25 | 16 | E | 13 | 37 |
| 1.5 | 150 | 16 | A | 36 | 18 |
| 1.5 | 150 | 16 | B | 32 | 23 |
| 1.5 | 150 | 16 | C | 22 | 28 |
| 1.5 | 150 | 16 | D | 7 | 34 |
| 1.5 | 150 | 16 | E | 0 | 33 |
| 1.5 | 100 | 16 | A | 73 | 10 |
| 1.5 | 100 | 16 | B | 28 | 41 |
| 1.5 | 100 | 16 | C | 5 | 46 |
| 1.5 | 100 | 16 | D | 4 | 45 |
| 1.5 | 100 | 16 | E | 0 | 22 |
| 1.5 | 50 | 16 | A | 49 | 16 |
| 1.5 | 50 | 16 | B | 23 | 41 |
| 1.5 | 50 | 16 | C | 47 | 23 |
| 1.5 | 50 | 16 | D | 3 | 43 |
| 1.5 | 50 | 16 | E | 1 | 36 |
| 1.5 | 25 | 16 | A | 75 | 12 |
| 1.5 | 25 | 16 | B | 76 | 0 |
| 1.5 | 25 | 16 | C | 45 | 19 |
| 1.5 | 25 | 16 | D | 17 | 45 |
| 1.5 | 25 | 16 | E | 1 | 34 |
| 0.5 | 150 | Tech. | A | 83 | 3 |
| 0.5 | 150 | Tech. | B | 93 | 0 |
| 0.5 | 150 | Tech. | C | 92 | 0 |
| 0.5 | 150 | Tech. | D | 87 | 3 |
| 0.5 | 150 | Tech. | E | 89 | 0 |
| 1.0 | 150 | Tech. | A | 87 | 0 |
| 1.0 | 150 | Tech. | B | 83 | 4 |
| 1.0 | 150 | Tech. | C | 87 | 3 |
| 1.0 | 150 | Tech. | D | 86 | 0 |
| 1.0 | 150 | Tech. | E | 64 | 18 |
| 1.5 | 150 | Tech. | A | 96 | 0 |
| 1.5 | 150 | Tech. | B | 100 | 0 |
| 1.5 | 150 | Tech. | C | 82 | 2 |
| 1.5 | 150 | Tech. | D | 80 | 0 |
| 1.5 | 150 | Tech. | E | 8 | 54 |

Test 23

Greenhouse tests of the compound of Example 10 were carried out on Waldron wheat, substantially as described above in Test 5. In this group of experiments, the compound was sometimes supplied as technical material, formulated substantially as described above in Test 3, and sometimes as a formulated aqueous suspension or wettable powder, the formulae of which are identified below. In some of the experiments, extra surfactant, polysorbate 20, was added to the final dispersion before spraying in the amount of 0.25%. Those experiments are identified in the table below by an x in the "surfactant" column.

The observed results were as follows.

TABLE 34

| Formulation | Surfactant | Concentration | Spikelets | Seed/ Spikelet |
|---|---|---|---|---|
| Tech. | | 1000 ppm. | 13.3 | 0.04 |
| Tech. | | 800 | 14.0 | 0.11 |
| Tech. | | 600 | 14.3 | 0.03 |
| Tech. | | 400 | 13.7 | 0.12 |
| Tech. | | 200 | 13.0 | 0.05 |
| Tech. | | 100 | 13.5 | 1.56 |
| 16 | | 1000 | 13.7 | 0.05 |
| 16 | | 800 | 14.3 | 0.03 |
| 16 | | 600 | 13.3 | 0.08 |
| 16 | | 400 | 13.3 | 0.09 |
| 16 | | 200 | 14.0 | 0.09 |
| 16 | | 100 | 12.8 | 1.06 |
| 17 | | 1000 | 13.7 | 0.16 |
| 17 | | 800 | 13.7 | 0.05 |
| 17 | | 600 | 15.0 | 0.02 |
| 17 | | 400 | 15.0 | 0.16 |
| 17 | | 200 | 13.3 | 0.26 |
| 17 | | 100 | 12.0 | 1.51 |
| Tech. | | 400 | 13.5 | 0.04 |
| Tech. | | 300 | 13.8 | 0.46 |
| Tech. | | 200 | 12.2 | 0.22 |
| Tech. | | 100 | 14.0 | 0.93 |
| Tech. | | 50 | 13.3 | 1.30 |
| Tech. | | 25 | N | |
| 16 | x | 400 | 16.0 | 0.02 |
| 16 | x | 300 | 13.4 | 0.25 |
| 16 | x | 200 | 14.6 | 0.34 |
| 16 | x | 100 | 15.0 | 0.49 |
| 16 | x | 50 | 15.0 | 1.13 |
| 16 | x | 25 | N | |
| 17 | x | 400 | 14.4 | 0.13 |
| 17 | x | 300 | 13.6 | 0.35 |
| 17 | x | 200 | 13.0 | 0.27 |
| 17 | x | 100 | 14.3 | 0.99 |
| 17 | x | 50 | N | |
| 17 | x | 25 | N | |
| 18 | | 400 | N | |
| 18 | | 200 | N | |
| 18 | | 100 | N | |
| 18 | | 50 | N | |
| 19 | | 400 | N | |
| 19 | | 200 | N | |
| 19 | | 100 | N | |
| 19 | | 50 | N | |
| 20 | | 400 | N | |
| 20 | | 200 | N | |
| 20 | | 100 | N | |
| 20 | | 50 | N | |
| 21 | | 400 | N | |
| 21 | | 200 | N | |
| 21 | | 100 | N | |
| 21 | | 50 | N | |
| 22 | | 400 | N | |
| 22 | | 200 | N | |
| 22 | | 100 | N | |
| 22 | | 50 | N | |
| 23 | | 400 | N | |
| 23 | | 200 | N | |
| 23 | | 100 | N | |
| 23 | | 50 | N | |

Test 24

Further experiments with the compound of Example 10 were carried out substantially as described in the test immediately above, except that polysorbate 20 was added to some of the spray dispersions as indicated in the Table below.

TABLE 35

| Formulation | surfactant | Concentration | Spikelets | Seed/ Spikelet |
|---|---|---|---|---|
| 18 | 0.5% polysorbate 20 | 400 ppm. | 13.3 | 0.38 |
| 18 | 0.5% polysorbate 20 | 200 | N | |
| 18 | 0.5% polysorbate 20 | 100 | N | |
| 18 | 0.5% polysorbate 20 | 50 | N | |
| 19 | 0.5% polysorbate 20 | 400 | 14.0 | 0.95 |
| 19 | 0.5% polysorbate 20 | 200 | N | |
| 19 | 0.5% polysorbate 20 | 100 | N | |
| 19 | 0.5% polysorbate 20 | 50 | N | |
| 20 | 0.5% polysorbate 20 | 400 | N | |
| 20 | 0.5% polysorbate 20 | 200 | N | |
| 20 | 0.5% polysorbate 20 | 100 | N | |
| 20 | 0.5% polysorbate 20 | 50 | N | |
| 21 | 0.5% polysorbate 20 | 400 | 12.0 | 0.23 |
| 21 | 0.5% polysorbate 20 | 200 | 12.0 | 0.75 |
| 21 | 0.5% polysorbate 20 | 100 | N | |
| 21 | 0.5% polysorbate 20 | 50 | N | |
| 22 | 0.5% polysorbate 20 | 400 | 11.0 | 0.14 |
| 22 | 0.5% polysorbate 20 | 200 | 12.7 | 0.27 |
| 22 | 0.5% polysorbate 20 | 100 | 12.0 | 0.48 |
| 22 | 0.5% polysorbate 20 | 50 | N | |
| 23 | 0.5% polysorbate 20 | 400 | 12.5 | 0.03 |
| 23 | 0.5% polysorbate 20 | 200 | 11.7 | 0.41 |
| 23 | 0.5% polysorbate 20 | 100 | 12.5 | 0.30 |
| 23 | 0.5% polysorbate 20 | 50 | N | |
| 17 | | 400 | N | |
| 17 | | 200 | N | |
| 17 | | 100 | N | |
| 17 | | 50 | N | |
| 24 | | 400 | N | |
| 24 | | 200 | N | |
| 24 | | 100 | N | |
| 24 | | 50 | N | |
| 25 | | 400 | N | |
| 25 | | 200 | N | |
| 25 | | 100 | N | |
| 25 | | 50 | N | |
| 16 | | 400 | N | |
| 16 | | 200 | N | |
| 16 | | 100 | N | |
| 16 | | 50 | N | |
| Tech. | | 400 | 14.2 | 0.07 |
| Tech. | | 400 | 14.0 | 0.48 |
| Tech. | | 200 | 13.5 | 0.10 |
| Tech. | | 200 | 13.0 | 0.17 |
| Tech. | | 100 | N | |
| Tech. | | 100 | N | |
| Tech. | | 50 | N | |
| Tech. | | 50 | N | |

Test 25

The experiments reported in this test were carried out in the same manner as those in the test immediately above, except that the compound in use was that of Example 1.

TABLE 36

| Formulation | Surfactant | Concentration | Spikelets | Seed/Spikelet |
|---|---|---|---|---|
| Tech. | | 2000 | 10.9 | 0.09 |
| Tech. | | 1500 | 12.3 | 0.15 |
| Tech. | | 1000 | 12.7 | 0.25 |
| Tech. | | 600 | 13.0 | 1.38 |
| Tech. | | 300 | 13.7 | 1.12 |
| Tech. | | 100 | 10.8 | 1.66 |
| 26 | | 2000 | 13.0 | 0.35 |
| 26 | | 1500 | 12.0 | 0.60 |
| 26 | | 1000 | 13.0 | 1.65 |
| 26 | | 600 | 12.2 | 1.73 |
| 26 | | 300 | 11.2 | 1.85 |
| 26 | | 100 | 11.5 | 1.98 |
| 26 | 0.25% polysorbate 20 | 2000 | 12.0 | 0.03 |
| 26 | 0.25% polysorbate 20 | 1500 | 12.5 | 0.09 |
| 26 | 0.25% polysorbate 20 | 1000 | 13.0 | 0.23 |
| 26 | 0.25% polysorbate 20 | 600 | 13.3 | 0.76 |
| 26 | 0.25% polysorbate 20 | 300 | 11.5 | 1.41 |
| 26 | 0.25% polysorbate 20 | 100 | 10.7 | 1.81 |
| 27 | | 2000 | 11.7 | 1.38 |
| 27 | | 1500 | 11.5 | 1.71 |
| 27 | | 1000 | 11.7 | 1.80 |
| 27 | | 600 | 11.7 | 1.86 |
| 27 | | 300 | 13.0 | 1.90 |
| 27 | | 100 | 11.3 | 1.87 |
| 27 | 0.25% polysorbate 20 | 2000 | 13.0 | 0.78 |
| 27 | 0.25% polysorbate 20 | 1500 | 13.3 | 0.32 |
| 27 | 0.25% polysorbate 20 | 1000 | 13.0 | 0.77 |
| 27 | 0.25% polysorbate 20 | 600 | 12.7 | 0.80 |
| 27 | 0.25% polysorbate 20 | 300 | 13.5 | 1.16 |
| 27 | 0.25% polysorbate 20 | 100 | 12.7 | 1.47 |
| 28 | | 1000 | N | |
| 28 | | 800 | N | |
| 28 | | 600 | N | |
| 28 | | 400 | N | |
| 28 | | 200 | N | |
| 28 | | 100 | N | |
| 29 | | 1000 | N | |
| 29 | | 800 | N | |
| 29 | | 600 | N | |
| 29 | | 400 | N | |
| 29 | | 200 | N | |
| 29 | | 100 | N | |

Test 26

The compound of Example 1 was formulated as 5% granular compositions, and was tested on Waldron wheat grown in the greenhouse in 4-inch pots. The compound was applied at the time the seeds were planted, and was incorporated in the soil around the seeds. The application rate of the compound is expressed as milligrams of compound per 4-inch pot.

TABLE 37

| Formulation | Rate, mg./pot | Spikelets | Seed/Spikelet |
|---|---|---|---|
| 30 | 20 | 12.0 | 0 |
| 30 | 10 | 11.7 | 0.28 |
| 30 | 5 | 13.7 | 0.23 |
| 31 | 20 | 13.2 | 0.03 |
| 31 | 10 | 12.0 | 0.25 |
| 31 | 5 | 12.0 | 0.38 |
| 32 | 20 | 11.3 | 0.43 |
| 32 | 10 | 12.5 | 0.22 |
| 32 | 5 | N | |

Test 27

The following experiments were carried out as described immediately above, except that the granular formulations were applied 14 days after planting, by sprinkling the formulation over the soil in the pots.

TABLE 38

| Formulation | Rate, mg./pot | Spikelets | Seed/Spikelet |
|---|---|---|---|
| 30 | 20 | 8.5 | 0 |
| 30 | 10 | 9.0 | 0 |
| 30 | 5 | 9.0 | 0.03 |
| 31 | 20 | 8.5 | 0 |
| 31 | 10 | 9.0 | 0 |
| 31 | 5 | 8.5 | 0.28 |
| 32 | 20 | 9.0 | 0 |
| 32 | 10 | 8.0 | 0.06 |
| 32 | 5 | 8.5 | 0 |

Test 28

Further experiments were carried out as described in Test 26 above, except that the wheat was planted in 8-inch pots, rather than in 4-inch pots.

TABLE 39

| Formulation | Rate, mg./pot | Spikelets | Seed/Spikelet |
|---|---|---|---|
| 30 | 40 | 12.0 | 0.08 |
| 30 | 40 | 12.0 | 0.04 |
| 30 | 20 | 13.0 | 0 |
| 30 | 20 | Herbicidal | |
| 30 | 5 | 12.0 | 0.58 |
| 30 | 5 | 11.3 | 0.47 |
| 31 | 40 | Herbicidal | |
| 31 | 40 | Herbicidal | |
| 31 | 20 | 12.0 | 0.08 |
| 31 | 20 | 12.0 | 0.08 |
| 31 | 5 | 10.0 | 0.30 |
| 31 | 5 | 12.0 | 0.42 |
| 32 | 40 | 11.0 | 0 |
| 32 | 40 | 9.0 | 0 |
| 32 | 20 | 11.0 | 0.05 |
| 32 | 20 | 10.0 | 0.10 |
| 32 | 5 | 11.3 | 0.82 |
| 32 | 5 | 14.0 | 0.93 |

Test 29

The compound of Example 10 was tested in field plots planted to barley of the varieties Pike and Barsoy. The barley was planted in late September, and was sprayed with aqueous dispersions, prepared substantially as described in Test 3 above, of the compound on Apr. 16, when the plants were growing briskly and their reproductive organs had begun to differentiate but the anthers had not yet been formed. Five treatment regimes were used, as explained in Test 20 above. The first application of compound was on Apr. 16, and the other two applications followed at intervals of 3–4 days. In all cases, 150 gal./acre of aqueous dispersion were applied.

Only the data at 3 lbs./acre of compound are shown in the table below, since no effect was obtained from tests at 0.5 and 1.0 lb./A.

TABLE 40

| Variety | Rate, lb./A. | Regime | Fertility | Hybrid |
|---|---|---|---|---|
| Pike | 3.0 | A | 100 | 0 |
| Pike | 3.0 | B | 100 | 0 |
| Pike | 3.0 | C | 100 | 0 |
| Pike | 3.0 | D | 100 | 0 |
| Pike | 3.0 | E | 100 | 0 |
| Barsoy | 3.0 | A | 100 | 0 |
| Barsoy | 3.0 | B | 100 | 0 |
| Barsoy | 3.0 | C | 100 | 0 |
| Barsoy | 3.0 | D | 2 | 99 |
| Barsoy | 3.0 | E | 16 | 85 |

Test 30

Barley seeds were planted in 8-inch pots in soil in which the compound of Example 10 had been incorporated, in the form of a formulation substantially as described in Test 3. The application rates are described in the table below. The plants were allowed to grow out in the greenhouse, and the seeds produced by the plants were counted with the following results.

TABLE 41

| lb./A | Spikelets | Seed/Spikelet |
|---|---|---|
| 1.0 | N | |
| 1.0 | 45.2 | 0.05 |
| 5.0 | 45.5 | 0.04 |
| 5.0 | 41.5 | 0.07 |
| 20.0 | 43.7 | 0 |
| 20.0 | 45.0 | 0 |
| 50.0 | 45.0 | 0 |
| 50.0 | 48.5 | 0 |
| Control | 44.0 | 0.86 |

Test 31

In this test, barley was planted in a soilless potting mix in 4-inch pots, and the plants were sprayed once with a dispersion of the compound of Example 10, prepared substantially as described in Test 3 above. The applications were made at three different times, as set out in the table below, and at various concentrations. Larger volumes of dispersion were applied in the later applications, to compensate for the larger volume of foliage of the plants.

TABLE 42

| Days after Planting | Concentration, ppm. | Spikelets | Seed/Spikelet |
|---|---|---|---|
| 11 | 1500 | 23.4 | 0.41 |
| 11 | 1000 | 25.8 | 0.36 |
| 11 | 600 | 28.8 | 0.51 |
| 11 | 200 | 28.2 | 0.79 |
| 11 | Control | 32.5 | 0.84 |
| 18 | 1500 | 22.8 | 0 |
| 18 | 1000 | 24.5 | 0 |
| 18 | 600 | 23.8 | 0 |
| 18 | 200 | 23.5 | 0 |
| 18 | Control | 24.0 | 0.70 |
| 25 | 1500 | 26.5 | 0.02 |
| 25 | 1000 | 24.8 | 0.08 |
| 25 | 600 | 27.2 | 0.05 |
| 25 | 200 | 27.0 | 0.04 |
| 25 | Control | 26.5 | 0.79 |

Test 32

The experiments of this test were carried out substantially as explained in Test 31 immediately above, except that two applications of the compound dispersion were made, 7 days apart. The date named in the table below is the date of the first application.

TABLE 43

| Days after Planting | Concentration, ppm. | Spikelets | Seed/Spikelet |
|---|---|---|---|
| 11 | 1500 | 26.5 | 0.05 |
| 11 | 1000 | 27.5 | 0 |
| 11 | 600 | 23.8 | 0.09 |
| 11 | 200 | 27.2 | 0 |
| 11 | Control | 31.0 | 0.87 |
| 18 | 1500 | 26.2 | 0 |
| 18 | 1000 | 23.8 | 0 |
| 18 | 600 | 20.0 | 0 |
| 18 | 200 | 20.0 | 0 |
| 18 | Control | 31.5 | 0.87 |
| 25 | 1500 | 23.0 | 0.06 |
| 25 | 1000 | 21.0 | 0.04 |
| 25 | 600 | 25.0 | 0.05 |
| 25 | 200 | 27.0 | 0 |
| 25 | Control | 32.2 | 0.75 |

Test 33

In these experiments, compound dispersions, prepared from the compound of Example 10 substantially as described in Test 3 above, were applied three times, at 7-day intervals, to barley plants growing in the greenhouse in 4-inch pots of soilless potting mixture. Different varieties of barley were used, and the age of the plants at the first application was also varied, as shown in the table below.

TABLE 44

| Variety | Days after Planting | Concentration, ppm. | Spikelets | Seed/Spikelet |
|---|---|---|---|---|
| Olli | 13 | 1500 | 24.5 | 0 |
| Olli | 13 | 1000 | 25.0 | 0 |
| Olli | 13 | 600 | 23.0 | 0 |
| Olli | 13 | 200 | 29.5 | 0 |
| Olli | 13 | Control | 33.6 | 0.74 |
| Gateway | 13 | 1500 | 22.5 | 0 |
| Gateway | 13 | 1000 | 19.0 | 0 |
| Gateway | 13 | 600 | 23.0 | 0 |
| Gateway | 13 | 200 | 20.5 | 0 |
| Gateway | 13 | Control | 25.8 | 0.51 |
| Larker | 22 | 1500 | 38.6 | 0.03 |
| Larker | 22 | 1000 | 38.8 | 0.02 |
| Larker | 22 | 600 | 37.8 | 0.08 |
| Larker | 22 | 200 | 39.5 | 0.11 |
| Larker | 22 | Control | 34.0 | 0.29 |

Test 34

Otal and Bonanza barley varieties were submitted to a test in which the compound of Example 10, formulated substantially as described in Test 3 above, was sprayed four times on the developing plants. The first application was made 13 days after planting, and the other three applications followed at 7-day intervals. The results were as follows.

TABLE 45

| Variety | Concentration, ppm | Spikelets | Seed/Spikelet |
|---|---|---|---|
| Otal | 1500 | 22.0 | 0.13 |
| Otal | 1000 | 29.0 | 0.44 |
| Otal | 600 | 19.2 | 0.14 |
| Otal | 200 | 30.5 | 0.51 |
| Otal | Control | 24.0 | 0.61 |
| Bonanza | 1500 | 30.0 | 0 |
| Bonanza | 1000 | 32.5 | 0 |
| Bonanza | 600 | 29.5 | 0 |
| Bonanza | 200 | 28.5 | 0.01 |

TABLE 45-continued

| Variety | Concentration, ppm | Spikelets | Seed/Spikelet |
|---|---|---|---|
| Bonanza | Control | 31.0 | 0.70 |

Test 35

Grain sorghum seeds of a hybrid variety were planted in 10-inch pots in soil in which the compound of Example 10, formulated as described in Test 3, had been incorporated. The compound was applied at the rate of 170 mg. per pot. The compound had no effect; the plants produced the normal amount of pollen and seeds.

Test 36

Grain sorghum was planted in 10-inch pots and grown in the greenhouse, and the compound of Example 10, formulated substantially as described in Test 3, was applied seven times to the plants, at intervals of about 1 week. The first application was made 33 days after planting the seed. Applications were made at 1500, 1000 and 600 ppm. concentration; all applications were ineffective, as the plants produced approximately the normal amounts of pollen and seeds.

Test 37

Seed of an unknown variety of oats was planted in 8-inch pots of soil in which the compound of Example 10, formulated substantially as described in Test 3, had been incorporated. The plants were allowed to grow in the greenhouse to maturity, and the number of seed produced by the plants were counted and are reported in the table below.

TABLE 46

| Rate, lb./A. | Spikelets | Seed/Spikelet |
|---|---|---|
| 1 | N | |
| 5 | N | |
| 20 | 45.3 | 0.14 |
| 50 | 52.1 | 0 |
| Control | 45.5 | 0.93 |

Test 38

Oats were grown in the greenhouse in 8-inch pots, and the plants were sprayed with aqueous dispersions of the compound of Example 10, substantially as described in Test 3 above. The first application to the plants was made 11 days after planting, and three more applications were made at 7-day intervals. The first application was of 3 ml., the second application, of 5 ml., and the last two, of 10 ml. each. Applications were made at 200, 600, 1000 and 1500 ppm. No effect was observed from any of the treatments, the plants produced the normal number of seeds.

Test 39

The compound of Example 1 was formulated substantially as described in Test 3, and was applied to oats plants growing in the greenhouse in 6-inch pots. Six applications were made to the plants; the first application was 18 days after planting, and the others followed at 7-day intervals. Applications were made both as soil drenches, consisting of 50 ml. of 1000 ppm. dispersion, and as foliar sprays at 800 and 1500 ppm. concentration. All treatments were ineffective; the plants produced the normal number of seeds in all cases.

Test 40

A number of compounds of the present invention were tested on rye of the variety Rymin, growing in 4-inch pots in the greenhouse. The compounds were applied three times, formulated substantially as described in Test 3 above; the first application was 20 days after planting, and the others followed at 7-day intervals. Various concentrations of the compounds were used, as set out in the table below, and the results were determined by counting the seeds as described in the tests above.

TABLE 47

| Compound of Example No. | Concentration, ppm. | Spikelets | Seed/Spikelet |
|---|---|---|---|
| 1 | 1500 | 18.8 | 0.74 |
| 1 | 1000 | 14.5 | 0.79 |
| 1 | 600 | 18.2 | 1.02 |
| 1 | 200 | 17.3 | 0.83 |
| 10 | 1500 | 16.9 | 0.80 |
| 10 | 1000 | 19.3 | 0.85 |
| 10 | 600 | 16.9 | 0.81 |
| 10 | 200 | 15.8 | 0.76 |
| 23 | 1500 | 16.0 | 0.64 |
| 23 | 1000 | 15.0 | 0.64 |
| 23 | 600 | 14.7 | 0.54 |
| 23 | 200 | 17.0 | 0.62 |
| 25 | 1500 | 18.8 | 0.53 |
| 25 | 1000 | 16.5 | 0.31 |
| 25 | 600 | 18.3 | 0.38 |
| 25 | 200 | 20.2 | 0.41 |
| Control | | 20.2 | 0.39 |

Test 41

Seeds of the Gazelle variety of rye were planted in 8-inch pots of soilless potting mixture, in which the compound of Example 10, formulated substantially as described in Test 3, had been incorporated. The plants were allowed to grow out in the greenhouse, and were bagged and the seeds counted as described in the tests above.

TABLE 48

| Rate, lb./A. | Spikelets | Seed/Spikelet |
|---|---|---|
| 1 | 28.7 | 0.36 |
| 1 | 29.3 | 0.58 |
| 5 | 32.0 | 0.69 |
| 5 | 26.0 | 0.35 |
| 20 | 34.0 | 0.74 |
| 20 | 29.0 | 0.72 |
| 50 | 33.0 | 0.70 |
| 50 | 37.0 | 0.68 |
| Control | 38.0 | 0.71 |
| Control | 33.0 | 0.82 |

Test 42

In this test, Gazelle rye plants were grown in the greenhouse, and were treated with foliar sprays of the compound of Example 10, formulated as described in Test 3 above. The first application was made 13 days after planting, and the second was 6 days thereafter.

TABLE 49

| Concentration ppm. | Spikelets | Seed/Spikelet |
|---|---|---|
| 3000 | 21.5 | 0.80 |
| 3000 | 26.0 | 0.67 |

TABLE 49-continued

| Concentration ppm. | Spikelets | Seed/Spikelet |
|---|---|---|
| 1000 | 28.5 | 0.69 |
| 1000 | 33.0 | 0.55 |
| 500 | 31.5 | 0.87 |
| 500 | 32.0 | 0.38 |
| Control | 30.5 | 0.94 |

Test 43

The compound of Example 10 was tested as a foliar spray on greenhouse-grown triticale. The plants were 13 days old when the first application was applied, and another application was made 6 days thereafter. The compound was formulated substantially as described in Test 3 above, and the following results were observed.

TABLE 50

| Concentration, ppm. | Spikelets | Seed/Spikelet |
|---|---|---|
| 3000 | 16.0 | 0.28 |
| 3000 | 18.0 | 0.13 |
| 1000 | 15.5 | 1.47 |
| 1000 | 18.0 | 2.06 |
| 500 | 13.3 | 0.60 |
| 500 | 17.0 | 2.00 |
| Control | 16.7 | 1.38 |

Test 44

The TL-419 variety of triticale was planted in 8-inch pots of soilless potting mixture in which the compound of Example 10, formulated substantially as in Test 3, had been incorporated. The results were as follows.

TABLE 51

| Rate, lb./A. | Spikelets | Seed/Spikelet |
|---|---|---|
| 50 | 18.0 | 1.33 |
| 50 | 20.0 | 1.21 |
| 20 | 21.5 | 1.05 |
| 20 | 18.5 | 1.49 |
| 5 | 18.5 | 1.74 |
| 5 | 21.0 | 1.60 |
| 1 | 21.0 | 1.79 |
| 1 | 20.0 | 1.66 |
| Control | 17.5 | 1.99 |
| Control | 17.0 | 1.97 |

Test 45

Rice seedlings of the Nato variety were planted in 1-gallon steel cans of soil, and the surface of the soil was covered with water to simulate rice paddy conditions. The plants were grown in a growth chamber and were foliar sprayed eight times with dispersions of the compound of Example 10, formulated substantially as described in Test 3. The first application was made 19 days after transplanting, and the other applications followed at 7-day intervals. The differentiation of the reproductive structures of the plant began between the fourth and fifth applications. The concentration of the dispersions were 200, 600, 1000 and 1500 ppm. The plants were bagged, and seeds were counted, as described in the tests above, and it was found that none of the treatments had any effect. All of the treated plants produced approximately the same number of seeds as did the control plants.

Test 46

Rice plants of the 201 variety were grown and treated substantially as described in the test above, except that four applications were made, the first of which was 25 days after transplanting, and only two concentrations were used, 1000 and 3000 ppm. The plants deteriorated, partially because of the amount and frequency of the applications of compound. The test was not completed because of the poor quality of the plants.

Test 47

Rice seedlings of the 201 variety were grown as described in Test 45, and were treated 21 days after transplanting with a soil drench of the compound of Example 10 at 50 and at 25 lb./A. The compound was formulated substantially as described in Test 3. The plants were grown in a growth chamber on 10 hour days at 28° daytime and 21° at night. The plants deteriorated, apparently because of phytotoxicity, and the test was not completed.

Other rice plants of the Nato variety were treated with the compound of Example 10 as a soil drench at 10 and at 5 lb./A. The treatments were applied when the head length of the plants was 3 mm.; the treatments were applied 50 days after the plants were transplanted. The treatments had no effect; the plants produced the normal number of seeds.

Test 48

Several compounds of the invention were tested on corn of the Gaspe Flint variety by incorporating the compounds, formulated substantially as in Test 3, in the soil in which the corn seeds were planted. Two plants were subjected to each treatment rate. The effect of the compounds was measured by observing the tassels of the mature plants, and rating the treatments as active if the tassels did not produce pollen. In the table below, active treatments are indicated by "A" and inactive ones by "N".

TABLE 52

| Compound of Example No. | Rate, lb./A | Effect |
|---|---|---|
| 1 | 15 | N |
| 1 | 15 | N |
| 1 | 5 | N |
| 1 | 5 | N |
| 1 | 1 | N |
| 1 | 1 | N |
| 10 | 15 | A |
| 10 | 15 | N |
| 10 | 5 | N |
| 10 | 5 | N |
| 10 | 1 | N |
| 10 | 1 | N |
| 14 | 15 | A |
| 14 | 15 | N |
| 14 | 5 | N |
| 14 | 5 | N |
| 14 | 1 | N |
| 14 | 1 | N |
| 19 | 15 | N |
| 19 | 15 | N |
| 19 | 5 | N |
| 19 | 5 | N |
| 19 | 1 | N |
| 19 | 1 | N |
| Control | | N |
| Control | | N |
| Control | | N |
| Control | | N |

Test 49

In this test, corn plants of the variety CM105 were treated with the compound of Example 10 by injecting an aqueous acetone solution of the compound directly into the stalks of the plants, immediately above the tassel node. The plants were injected 36 days after planting.

The effect of the treatments was determined by observing the ability of the pollen produced by the treated plants to grow in a growth medium composed of 0.6% agar, 50 ppm. boric acid, 600 ppm. calcium nitrate, and 15% sucrose at pH 7. A treatment was rated as active if the pollen produced by the treated plants was not viable. In this test, one plant which was injected with 6 mg. of the compound exhibited slight injury; five plants injected with 4 mg. of the compound were rated inactive.

Test 50

Corn seeds were planted in a 6-gallon container, in soil into which had been incorporated 312 mg. of the compound of Example 10, formulated substantially as described in Test 3. The application rate was approximately 10 lb./A. After the plants had germinated, they were sprayed with 1000 ppm. aqueous dispersions of the compound of Example 10, also formulated as in Test 3. The first application was applied 13 days after planting, and six additional treatments were made at 7-day intervals. Pollen of the treated plants was transferred to control plants, resulting in complete seed set. The treatments, therefore, were apparently ineffective.

Test 51

A single foliar spray of the compound of Example 10, formulated as in Test 3 above, was made to corn plants, 28 days after planting the seeds. The concentration of the spray dispersion was 2000 ppm. Pollen of the treated plants was observed for its viability in growth medium, and the treatment was found to be ineffective.

In another experiment, a single application was made to corn plants 15 days after planting, at 200, 600, 1000, 1500 and 2000 ppm. All treatments were determined to be ineffective by observing the viability of pollen in growth medium.

Test 52

Corn plants were treated five times with the compound of Example 1, at 7-day intervals. Soil-drench applications were made by applying 150 ml. of 1000 ppm. dispersion to each 6-gallon container, and foliar spray applications were made with 10 ml. of 2000 ppm. concentration dispersion at each treatment. The effect of the treatments was determined by counting the percent germination of pollen grains dispersed in the growth medium described in Test 49 above, with the following results.

TABLE 53

| Treatment | % Germination |
| --- | --- |
| Drench | 25 |
| Drench | 32 |
| Spray | 28 |
| Spray | 35 |
| Control | 29 |
| Control | 35 |
| Control | 30 |
| Control | 30 |

Test 53

Golden Midget corn seeds were planted in soil in which the compound of Example 10 had been incorporated at various rates as shown below. The plants were allowed to grow out in the greenhouse, and pollen was collected and its germination was observed as described in the tests above. The results were as follows.

TABLE 54

| Rate, lb./A. | % Germination |
| --- | --- |
| 1 | 62 |
| 1 | 45 |
| 5 | 34 |
| 5 | 40 |
| 20 | 46 |
| 20 | 54 |
| 50 | 40 |
| 50 | 51 |
| Control | 60 |
| Control | 42 |

Test 54

The experiments reported here were carried out as was Test 53, except that the corn was of the Gaspe Flint variety.

TABLE 55

| Rate, lb./A. | % Germination |
| --- | --- |
| 1 | 50 |
| 1 | 42 |
| 5 | 52 |
| 5 | 48 |
| 20 | 37 |
| 20 | 41 |
| 50 | 45 |
| 50 | 30 |
| Control | 57 |
| Control | 34 |

The preferred compounds of the present invention, which are also the preferred compounds for the practice of the present pollen formation-inhibiting methods, are 4-carboxy-1-(3-chlorophenyl)-5-pyrazolecarboxamide, 4-carboxy-1-(3-methylphenyl)-5-pyrazolecarboxamide, 4-carboxy-1-(3-ethylphenyl)-5-pyrazolecarboxamide, 4-carboxy-1-(3,4-dichlorophenyl)-5-pyrazolecarboxamide, and 4-carboxy-1-(3-methoxyphenyl)-5-pyrazolecarboxamide. The alkali metal salts, ammonium salts and mono, di and tri($C_1$-$C_4$ alkyl)amine salts of the compounds just named are also preferred compounds of the invention.

The compounds of this invention are useful for inhibiting pollen formation in cereal grain plants which are sensitive to such treatment, and the compositions in which the compounds are formulated for application, and the methods by which the compounds are applied to obtain the inhibition of pollen formation, constitute embodiments of the invention.

A compound must be supplied to the plant before the formation of anthers. It must be noted that the head of a plant matures over a period of time, and different plants in a field mature at different times. Accordingly, a compound must be supplied before anther formation in the most mature plants in the field to be treated, if best results are to be obtained.

In wheat and barley, anther formation occurs while the plant's head is still near ground level, and is about 2 mm. long, and the plant has about 4 to 5 true leaves. Thus, it is advisable to dissect representative plants from time to time to determine when development of the head, and therefore of the anthers, is approaching. Best results are obtained by supplying the compound when the head is only a few mm. long. Comparable indications of development in other species are used to determine the proper time for treatment.

The compound must be supplied, not merely applied, to the plant before anther formation. In this document, the term "supplying" is used to mean administering the compound in such a manner that it is absorbed by the plant and is available to the target organs.

In all cases, the compound must be applied sufficiently early that it is absorbed and supplied to the plant before anther formation.

In the practice of the present invention, it is necessary to apply an effective amount of a compound of the invention to the plant or the soil in which it grows. Effective amounts can be measured in terms of the concentration of the compound in a dispersion, when the compound is applied to the foliage, or, preferably, can be measured in terms of the amount of compound applied per unit area of land. The concentration of the compound is a useful measurement, because the amount of compound applied to foliage is limited by the amount of the dispersion which is retained by the foliage. That amount is substantially constant, for a given size of plant, and therefore the amount of compound applied by that means can be increased only by increasing the concentration of the dispersion. Depending on the circumstances, effective concentrations of compounds range from about 100 to about 2000 parts per million by weight. Factors which affect the effective amount include the succulence of the foliage, the rate at which it is growing, and the weather at the time of application. In general, preferred concentrations for foliar applications are in the range from about 500 to about 1500 parts per million by weight.

Measurement of the amount of compound applied as a dose per unit area of land may be used for either application to the soil or application to the foliage. Of course, it will be understood that application to the foliage results in some soil application in all cases, since not all of the composition applied to the foliage adheres there. In general, rates of from about 1 to about 40 pounds of compound per acre of crop land are useful. It is more preferred to use rates from about 1 to about 20 pounds per acre, most preferably, from about 1 to about 10 pounds per acre of the most preferred compounds.

It has been observed that application of the compound in multiple doses provides better effectiveness, and there is some indication that a smaller total amount of compound can effectively be used when applied in multiple doses. It may be that the result is explained by the fact that not all plants form anthers at the same time, and multiple applications avoid the necessity for compounds to be stored for a long period in the plant or soil. Application of a compound from 2 to 4 times, at intervals of 3 to 10 days, is preferred.

More particularly, application of a compound of the invention from 2 to 3 times, where each application is of from about ½ to about 3 pounds of compound per acre, applied to the foliage, is particularly preferred. Further, application of the compound from 2 to 3 times, where each application is of a dispersion containing from about 200 to about 1000 parts per million by weight of compound, and the dispersion is applied so as to cover the foliage of the plants, is also preferred.

Another particularly preferred method of application of a compound of the invention is application to the soil in which the plants grow at a rate of from about 1 to about 10 pounds of compound per acre, applied once.

The plants to which a compound of the present invention may be applied to inhibit pollen formation are the cereal grain plants, including wheat, barley, corn, oats, rye, rice, sorghum and triticale. A preferred group of species include wheat, barley, rye and triticale. The more preferred species of plants are wheat and barley, and the most preferred species is wheat.

More particularly, the plants to which the invention is applied are defined as those which are sensitive to such treatment; that is, those in which the compounds will inhibit pollen formation when properly applied. The plants are defined in that manner because considerable variation in activity between varieties, and between individuals within a variety, has been observed. In barley, for example, some varieties require several times as much compound for activity as do other varieties. On the other hand, the varietal difference in activity in wheat is relatively small.

In other species, of which corn is a particularly good example, the differences in sensitivity to the compounds are more subtle than varietal differences. In corn, individual sensitive plants have been observed, although no variety wherein all plants are sensitive has been found. It is therefore necessary, in such a species, to screen for sensitive plants, and to use the seed produced by those plants to create a variety of sensitive plants for further use in hybridization.

Of course, some experimentation is needed to use the present invention properly, particularly in species such as corn. The experimentation, however, is well understood and routinely carried out by plant breeders. The nature of the tests is clearly shown above in the test portion of this document, and so the skilled reader can readily plan routine experiments which will identify sensitive plants or varieties and determine the proper application rate of a compound, by the ordinary skills of the art, and the teaching in this document.

A further aspect of the present invention is the production of hybrid seed by use of the present pollen formation inhibiting method. Seed of the varieties which will be the male and female parents is planted in separate but adjacent plots. The female parent variety, of course, must be sensitive to the treatment of the present invention. The size and location of the plots may be important. Some species, such as wheat and barley, do not produce great quantities of pollen, as corn does, and so the pollen cannot be expected to travel very far and still fertilize a high percentage of the female plants. Therefore, the female plots should be relatively narrow. For example, the female and male parent seed may usefully be planted in long alternate plots, only a few rows wide, with their long axes oriented across the prevailing wind.

It has been observed to be advantageous to plant the female parent variety seed densely enough to inhibit the plants from developing tillers. The reason is that tillers develop later than the main plants, and therefore their presence confuses the determination of the proper time to apply the compound.

At the proper time, as discussed above in detail, the compound is applied to the female parent plots to inhibit those plants from producing pollen. Those plants are then pollinated by the male parent plants and produce hybrid seed, which is harvested in the usual ways.

The compositions in which a compound of the present invention may be formulated are of many types. Since the compounds are effective when applied both to the foliage of the plants, and to the soil in which the plants grow, substantially all of the physical types of agricultural chemical compositions may be used.

Most economical and preferred compositions are concentrated water-emulsifiable or water-dispersable compositions. Such compositions include, in general, emulsifiable concentrates, suspension concentrates and wettable powders and granules, all of which are common in the agricultural chemical art. Some discussion of them will be provided, however, to assure complete understanding.

The concentration of a compound in a concentrated composition is entirely irrelevant to the use of the compound. Such compositions are diluted in water for application, and the application rate of the compound is determined by the ratio at which the composition is diluted in water, or by the amount of the composition which is applied per area of crop land. Thus, any desired application rate can be obtained from any concentrated composition. Farmers and agricultural chemists are acquainted with the simple calculations which are necessary.

Emulsifiable concentrates of the compounds comprise a convenient concentration of the compound dissolved in a phytologically-acceptable diluent which is a mixture of water-miscible organic solvent and emulsifiers. Useful organic solvents, in general, include aromatics, especially xylenes, and the petroleum fractions, especially the napthalenic and olefinic portions of petroleum, such as those called heavy aromatic naphthas. Terpenic solvents including rosin derivatives, and complex alcohols such as 2-ethoxyethanol are also often used, and amides such as dimethylacetamide may be particularly useful with the present compounds. Suitable emulsifiers for emulsifiable concentrates, generally used in amounts in the range of from about 1% to about 10% by weight of the concentrate, are frequently found among the alkylbenzenesulfonates, the alkyl sulfates, the non-ionics such as ethylene oxide adducts of alkyl phenol, and especially among the metal and amine salts of alkyl sulfates.

Wettable powders comprise an intimate mixture of the compound and a phytologically-acceptable diluent made up of an inert carrier and surfactants. The inert carrier is usually chosen from among easily water-dispersable powdery substances such as attapulgite clay, the montmorillonite clays, the diatomaceous earths and the purified silicates. Surfactants for wettable powders are found among the same types just mentioned for emulsifiable concentrates, as well as the sulfonated lignins and the naphthalenesulfonates. It is possible to compact a wettable powder into granular form, and thereby to produce a wettable granule, which has the advantage of being non-dusty and easy to measure and pour. When added to water, a properly formulated wettable granular product will disperse and become a fine suspension.

The compounds may also be formulated as suspensions, which consist of a relatively high concentration, in the interest of economy, of the compound in finely powdered form, dispersed and suspended in a phytologically-acceptable aqueous diluent. A surfactant system for a suspension product is much like that used in a wettable powder, but it must be capable of maintaining the compound in dispersed form over a long period of time. It is sometimes advisable to adjust the density of the liquid, as by dissolving an inert salt in it, in order to assist in the suspension of the relatively dense particles of compound.

When an aqueous dispersion of a compound, prepared by the dilution of a concentrated composition, is to be applied to foliage, an adjuvant is often used to improve the ability of the dispersion to wet and adhere to the foliage. Such adjuvants as vegetable gums, emulsified polybutenes, cationic and other surfactants and lignin derivatives are often used. The use of an adjuvant in aqueous dispersions of the present compounds is highly preferred, and regularly improves results. Not only the commercial adjuvants, which are commonly known to growers, but also ordinary surfactants, are beneficially used, at concentrations in the range of a few tenths of a percent in the dispersion.

Aqueous dispersions of concentrated compositions may be applied either to foliage or to the soil in which plants grow. When the application is to be to the soil, a granular composition can also be effectively used. A granular agricultural composition consists of the compound, applied, usually in a relatively low concentration such as from about 1 to about 10% by weight, to a granular carrier having a convenient particle size for application. Typically, the particle size range is from 20 to 60 mesh, on the standard U.S. sieve size scale. Such carriers as clay, sand, pulverized stone, corncob grits and the like are frequently used and may be chosen for convenience and economy. It is usually unnecessary to use any adjuvant or other ingredient other than the compound and the carrier, with perhaps a small amount of solvent in which the compound is applied to the carrier. The carrier may also be supplied in powdered form, and formulated by mixing the powdered carrier with the powdered compound and then compacting the mixture and granulating it to the desired particle size range.

The following specific examples of formulations of compounds of the present invention are provided to assist the reader. It will be understood that the following formulations, all of which were used in the tests described above in the specification, are merely exemplary of the manners of formulating the compounds. An agricultural chemist, using the following formulations as guides, can readily prepare any desired type of formulation, using any of the compounds of the invention as the active ingredient.

| | Formulation 1<br>0.4% Granules | Formulation 2<br>1% Granules | Formulation 3<br>1.2% Granules |
|---|---|---|---|
| compound of Example 1 | 0.4% | 1.03% | 1.24% |
| 30/60 mesh attapulgite | 99.6% | 98.97% | 98.76% |

| | Formulation 4<br>2% Granules | Formulation 5<br>3% Granules | Formulation 6<br>4% Granules |
|---|---|---|---|
| compound of Example 1 | 2.06% | 3.09% | 4.12% |
| 30/60 mesh attapulgite | 97.94% | 96.91% | 95.88% |

| | Formulation 7<br>5% Granules | Formulation 8<br>6% Granules | Formulation 9<br>10% Granules | Formulation 10<br>15% Granules |
|---|---|---|---|---|
| compound of Example 1 | 5.15% | 6.19% | 10.31% | 15.46% |
| 30/60 mesh | 94.85% | 93.81% | 89.69% | 84.54% |

-continued attapulgite

|  | Formulation 11 0.5% Granules | Formulation 12 1.5% Granules | Formulation 13 2.5% Granules | Formulation 14 3.75% Granules |
| --- | --- | --- | --- | --- |
| compound of Example 10 | 0.52% | 1.55% | 2.58% | 3.75% |
| 30/60 mesh attapulgite | 99.48% | 98.45% | 97.42% | 96.13% |

All of formulations 1–14 were prepared by dissolving the compound in an appropriate amount of dimethylformamide and impregnating the carrier with the solution. The solvent was then evaporated, at high temperature if necessary.

| Formulation 15 1 lb./gal. Suspension | |
| --- | --- |
| compound of Example 10 | 12.1% |
| Pluronic P-104 (non-ionic surfactant) | 1.0% |
| silicone antifoam | 0.2% |
| propylene glycol | 6.0% |
| magnesium aluminum silicate | 1.0% |
| xanthan gum | 0.1% |
| water | 79.6% |

The compound was ground with the P-104, the antifoam and part of the water in an attrition mill for 45 minutes, and was then mixed with the rest of the ingredients.

| Formulation 16 25% Wettable Powder | |
| --- | --- |
| compound of Example 10 | 26.9% |
| sodium salt of lignin with anionic wetting agents | 10.0% |
| purified silica | 10.0% |
| kaolin clay | 53.1% |

The above ingredients were thoroughly mixed, and the mixture was then milled through a hammermill and then through an air impact mill.

| Formulation 17 0.5 lb./gal. Suspension | |
| --- | --- |
| compound of Example 10 | 6.2% |
| Tergitol TMN-6 (non-ionic surfactant) | 5.0% |
| purified silica | 0.5% |
| silicone antifoam | 0.1% |
| 2% xanthan gum | 5.0% |
| water | 83.2% |

The compound was ground with part of the water, the silica and the antifoam in an attrition mill until 50% of the particles were smaller than 1 micron by microscopic inspection, and the suspension was then mixed with the rest of the ingredients.

| Formulation 18 1 lb./gal. Suspension | |
| --- | --- |
| compound of Example 10 | 12.1% |
| Tergitol TMN-6 | 1.0% |
| Polyfon H (lignin sulfonate salt) | 2.0% |
| 5% magnesium aluminum silicate suspension | 20.0% |
| 2% xanthan gum suspension | 5.0% |
| silicone antifoam | 0.2% |
| water | 59.7% |

The compound was ground in an attrition mill with the Tergitol, the Polyfon and part of the water, and was then mixed with the rest of the ingredients.

| Formulation 19 1 lb./gal. Suspension | |
| --- | --- |
| compound of Example 10 | 12.1% |
| Tergitol TMN-6 | 1.0% |
| Polyfon H | 2.0% |
| 5% magnesium aluminum silicate suspension | 20.0% |
| 2% xanthan gum suspension | 5.0% |
| propylene glycol | 6.0% |
| silicone antifoam | 0.2% |
| water | 53.7% |

The compound was ground in an attrition mill with the Tergitol, the Polyfon and part of the water, and was then mixed with the rest of the ingredients.

| Formulation 20 1 lb./gal. Suspension | |
| --- | --- |
| compound of Example 10 | 12.1% |
| Makon 12 (non-ionic surfactant) | 1.0% |
| 5% magnesium aluminum silicate suspension | 20.0% |
| 2% xanthan gum suspension | 5.0% |
| silicone antifoam | 0.2% |
| water | 61.7% |

The compound was ground in an attrition mill with the Makon, the antifoam and part of the water and was then mixed with the rest of the ingredients.

| Formulation 21 1 lb./gal. Suspension | |
| --- | --- |
| compound of Example 10 | 12.1% |
| Makon 12 | 1.0% |
| propylene glycol | 6.0% |
| 5% magnesium aluminum silicate suspension | 20.0% |
| 2% xanthan gum suspension | 5.0% |
| silicone antifoam | 0.2% |
| water | 55.7% | the compound was ground in an attrition mill with the Makon, the antifoam and part of the water, and was then mixed with the rest of the ingredients.

| Formulation 22 1 lb./gal. Suspension | |
| --- | --- |
| compound of Example 10 | 12.1% |
| Pluronic P-104 | 1.0% |
| 5% magnesium aluminum silicate suspension | 20.0% |
| 2% xanthan gum suspension | 5.0% |
| silicone antifoam | 0.2% |
| water | 61.7% |

The compound was ground in an attrition mill with the Pluronic, the antifoam and part of the water, and was then mixed with the rest of the ingredients.

| Formulation 23 1 lb./gal. Suspension | |
|---|---|
| compound of Example 10 | 12.1% |
| Pluronic P-104 | 1.0% |
| 5% magnesium aluminum silicate suspension | 20.0% |
| 2% xanthan gum suspension | 5.0% |
| silicone antifoam | 0.2% |
| propylene glycol | 6.0% |
| water | 55.7% |

The compound was ground in an attrition mill with the Pluronic, the antifoam and part of the water, and was then mixed with the rest of the ingredients.

| Formulation 24 1 lb./gal. Suspension | |
|---|---|
| compound of Example 1 | 12.1% |
| Makon 12 | 5.0% |
| propylene glycol | 6.0% |
| magnesium aluminum silicate | 1.0% |
| xanthan gum suspension | 0.1% |
| silicone antifoam | 0.2% |
| water | 75.6% |

The compound was ground with the Makon, the antifoam and part of the water, and was then mixed with the rest of the ingredients.

| Formulation 25 1 lb./gal. Suspension | |
|---|---|
| compound of Example 10 | 12.1% |
| Makon 12 | 10.0% |
| propylene glycol | 6.0% |
| magnesium aluminum silicate | 1.0% |
| xanthan gum suspension | 0.1% |
| silicone antifoam | 0.2% |
| water | 70.6% |

The compound was ground in an attrition mill with half of the Makon, the antifoam and part of the water, and was then mixed with the rest of the ingredients.

| Formulation 26 1 lb./gal. Suspension | |
|---|---|
| compound of Example 1 | 12.2% |
| Tergitol TMN-6 | 10.0% |
| purified silica | 1.0% |
| 2% xanthan gum suspension | 10.0% |
| silicone antifoam | 0.2% |
| Polyfon H | 0.3% |
| water | 66.3% |

The compound was ground in an attrition mill with the silica, the Tergitol and part of the water until the size of 50% of the particles was smaller than 1.9 microns by Coulter Counter. The ground suspension was then mixed with the rest of the ingredients.

| Formulation 27 25% wettable powder | |
|---|---|
| compound of Example 1 | 25.8% |
| sodium salt of lignin plus anionic wetting agents | 10.0% |

| Formulation 27 (continued) 25% wettable powder | |
|---|---|
| purified silica | 10.0% |
| kaolin clay | 54.2 |

The mixture was ground through a laboratory-size air impact mill until the size of 50% of the particles was smaller than 4.1 microns by Coulter Counter.

| Formulation 28 5% Suspension | |
|---|---|
| compound of Example 1 | 5.0% |
| sodium napthaleneformaldehyde condensate | 3.0% |
| 30% formaldehyde | 0.4% |
| xanthan gum | 0.4% |
| propylene glycol | 5.0% |
| water | 86.2% |

The mixture was ground until the average particle size was 3 microns.

| Formulation 29 | |
|---|---|
| 5% Suspension | |

This formulation was identical to that of Formulation 28, except that the mixture was ground only until the average particle size was 6 microns.

| Formulation 30 5% Granules | |
|---|---|
| compound of Example 1 | 5.0% |
| 25/50 mesh attapulgite | 95.0% |
| Formulation 31 5% Granules | |
| compound of Example 1 | 5.0% |
| dye | 1.0% |
| 25/50 mesh attapulgite | 94.0% |
| Formulation 32 5% Granules | |
| compound of Example 1 | 5.0% |
| sand | 95.0% |

All of Formulations 30–32 were prepared by dissolving the compound in N-methylpyrrolidone, mixing the appropriate amount of the solution with the carrier, and evaporating the solvent.

We claim:

1. A compound of the formula

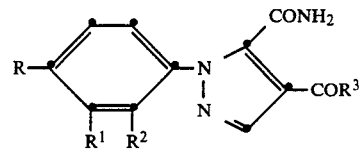

wherein R, $R^1$ and $R^2$ independently represent chloro, bromo, fluoro, $C_1$–$C_3$ alkoxy, $C_1$–$C_4$ alkyl or hydrogen, provided that at least one of R, $R^1$ and $R^2$ represents hydrogen, and further provided that $R^2$ may represent a group other than hydrogen only when one of R and $R^1$, but not both, represents a group other than hydrogen; $R^3$ represents hydroxy, methoxy, ethoxy, allyloxy or a phytologically-acceptable moiety forming a salt of the carboxylic acid.

2. A compound of claim 1 wherein $R^3$ represents hydroxy or a phytologically-acceptable moiety forming a salt of the carboxylic acid.

3. A compound of claim 1 wherein R and $R^2$ represent hydrogen.

4. A compound of claim 2 wherein R and $R^2$ represent hydrogen.

5. A compound of claim 1 wherein R and $R^1$ independently represent chloro, ethyl, bromo, methoxy or methyl.

6. A compound of claim 2 wherein R and $R^1$ independently represent chloro, ethyl, bromo, methoxy or methyl.

7. A compound of claim 3 wherein $R^1$ represents chloro, bromo, fluoro, $C_1$–$C_2$ alkyl or $C_1$–$C_2$ alkoxy.

8. A compound of claim 4 wherein $R^1$ represents chloro, bromo, fluoro, $C_1$–$C_2$ alkyl or $C_1$–$C_2$ alkoxy.

9. A compound of claim 3 wherein $R^1$ represents chloro, methoxy, ethyl or methyl.

10. A compound of claim 4 wherein $R^1$ represents chloro, methoxy, ethyl or methyl.

11. A compound of claim 3 wherein $R^1$ represents chloro, bromo or methyl.

12. A compound of claim 4 wherein $R^1$ represents chloro, bromo or methyl.

13. The compound of claim 1 which is 4-carboxy-1-(3-chlorophenyl)-5-pyrazolecarboxamide or a salt thereof.

14. The compound of claim 1 which is 4-carboxy-1-(3-methylphenyl)-5-pyrazolecarboxamide or a salt thereof.

15. The compound of claim 1 which is 4-carboxy-1-(3,4-dichlorophenyl)-5-pyrazolecarboxamide or a salt thereof.

16. The compound of claim 1 which is 4-carboxy-1-(3-ethylphenyl)-5-pyrazolecarboxamide or a salt thereof.

17. The compound of claim 1 which is 4-carboxy-1-(3-methoxyphenyl)-5-pyrazolecarboxamide or a salt thereof.

18. A pollen formation inhibiting composition comprising one or more phytologically-acceptable diluents and an amount of a compound of claim 1 effective to inhibit pollen formation.

19. A composition of claim 18 wherein the compound is a compound wherein $R^3$ represents hydroxy or a phytologically-acceptable moiety forming a salt of the carboxylic acid.

20. A composition of claim 18 wherein the compound is a compound wherein R and $R^2$ represent hydrogen.

21. A composition of claim 19 wherein the compound is a compound wherein R and $R^2$ represent hydrogen.

22. A composition of claim 18 wherein the compound is a compound wherein R and $R^1$ independently represent chloro, ethyl, bromo, methoxy or methyl.

23. A composition of claim 19 wherein the compound is a compound wherein R and $R^1$ independently represent chloro, ethyl, bromo, methoxy or methyl.

24. A composition of claim 20 wherein the compound is a compound wherein $R^1$ represents chloro, bromo, fluoro, $C_1$–$C_2$ alkyl or $C_1$–$C_2$ alkoxy.

25. A composition of claim 21 wherein the compound is a compound wherein $R^1$ represents chloro, bromo, fluoro, $C_1$–$C_2$ alkyl or $C_1$–$C_2$ alkoxy.

26. A composition of claim 20 wherein the compound is a compound wherein $R^1$ represents chloro, methoxy, ethyl or methyl.

27. A composition of claim 21 wherein the compound is a compound wherein $R^1$ represents chloro, methoxy, ethyl or methyl.

28. A composition of claim 20 wherein the compound is a compound wherein $R^1$ represents chloro, bromo or methyl.

29. A composition of claim 21 wherein the compound is a compound wherein $R^1$ represents chloro, bromo or methyl.

30. The composition of claim 18 wherein the compound is 4-carboxy-1-(3-chlorophenyl)-5-pyrazolecarboxamide or a salt thereof.

31. The composition of claim 18 wherein the compound is 4-carboxy-1-(3-methylphenyl)-5-pyrazolecarboxamide or a salt thereof.

32. The composition of claim 18 wherein the compound is 4-carboxy-1-(3,4-dichlorophenyl)-5-pyrazolecarboxamide or a salt thereof.

33. The composition of claim 18 wherein the compound is 4-carboxy-1-(3-ethylphenyl)-5-pyrazolecarboxamide or a salt thereof.

34. The composition of claim 18 wherein the compound is 4-carboxy-1-(3-methoxyphenyl)-5-pyrazolecarboxamide or a salt thereof.

35. A method of inhibiting pollen formation in a cereal grain plant which is sensitive to such treatment comprising supplying to the plant at a time prior to anther formation a pollen formation inhibiting amount of a compound of claim 1.

36. A method of claim 35 wherein the plant is a wheat or barley plant.

37. A method of claim 36 wherein the plant is a wheat plant.

38. A method of claim 35 wherein the compound is applied in a concentration of from about 100 to about 2000 ppm.

39. A method of claim 36 wherein the compound is applied in a concentration of from about 100 to about 2000 ppm.

40. A method of claim 35 wherein the compound is applied from about 2 to about 3 times, at a concentration of from about 200 to about 1000 ppm.

41. A method of claim 36 wherein the compound is applied from about 2 to about 3 times, at a concentration of from about 200 to about 1000 ppm.

42. A method of claim 35 wherein the compound is applied in an amount of from about 1 to about 40 pounds per acre.

43. A method of claim 36 wherein the compound is applied in an amount of from about 1 to about 40 pounds per acre.

44. A method of claim 35 wherein the compound is applied in an amount of from about 1 to about 20 pounds per acre.

45. A method of claim 36 wherein the compound is applied in an amount of from about 1 to about 20 pounds per acre.

46. A method of claim 35 wherein the compound is applied from about 2 to about 3 times in an amount of from about ½ to about 3 pounds per acre at each application.

47. A method of claim 36 wherein the compound is applied from about 2 to about 3 times in an amount of from about ½ to about 3 pounds per acre at each application.

48. A method of claim 35 wherein the compound is applied once to the soil in an amount of from about 1 to about 10 pounds per acre.

49. A method of claim 35 wherein the compound is a compound wherein $R^3$ represents hydroxy or a phytologically-acceptable moiety forming a salt of the carboxylic acid.

50. A method of claim 40 wherein the compound is a compound wherein $R^3$ represents hydroxy or a phytologically-acceptable moiety forming a salt of the carboxylic acid.

51. A method of claim 46 wherein the compound is a compound wherein $R^3$ represents hydroxy or a phytologically-acceptable moiety forming a salt of the carboxylic acid.

52. A method of claim 49 wherein the compound is a compound wherein R and $R^2$ represent hydrogen and $R^1$ represents chloro, methoxy, ethyl or methyl.

53. A method of claim 36 wherein the compound is a compound wherein $R^3$ represents hydroxy or a phytologically-acceptable moiety forming a salt of the carboxylic acid, R and $R^2$ represent hydrogen and $R^1$ represents chloro, methoxy, ethyl or methyl.

54. A method of claim 40 wherein the compound is a compound wherein $R^3$ represents hydroxy or a phytologically-acceptable moiety forming a salt of the carboxylic acid, R and $R^2$ represent hydrogen and $R^1$ represents chloro, methoxy, ethyl or methyl.

55. A method of claim 44 wherein the compound is a compound wherein $R^3$ represents hydroxy or a phytologically-acceptable moiety forming a salt of the carboxylic acid, R and $R^2$ represent hydrogen and $R^1$ represents chloro, methoxy, ethyl or methyl.

56. A method of claim 46 wherein the compound is a compound wherein $R^3$ represents hydroxy or a phytologically-acceptable moiety forming a salt of the carboxylic acid, R and $R^2$ represent hydrogen and $R^1$ represents chloro, methoxy, ethyl or methyl.

57. A method of claim 48 wherein the compound is a compound wherein $R^3$ represents hydroxy or a phytologically-acceptable moiety forming a salt of the carboxylic acid, R and $R^2$ represent hydrogen and $R^1$ represents chloro, methoxy ethyl or methyl.

58. A method of claim 36 wherein the compound is 4-carboxy-1-(3-chlorophenyl)-5-pyrazolecarboxamide or a salt thereof.

59. A method of claim 41 wherein the compound is 4-carboxy-1-(3-chlorophenyl)-5-pyrazolecarboxamide or a salt thereof.

60. A method of claim 47 wherein the compound is 4-carboxy-1-(3-chlorophenyl)-5-pyrazolecarboxamide or a salt thereof.

61. A method of claim 35 wherein the compound is 4-carboxy-1-(3-methylphenyl)-5-pyrazolecarboxamide or a salt thereof.

62. A method of claim 36 wherein the compound is 4-carboxy-1-(3-methylphenyl)-5-pyrazolecarboxamide or a salt thereof.

63. A method of claim 40 wherein the compound is 4-carboxy-1-(3-methylphenyl)-5-pyrazolecarboxamide or a salt thereof.

64. A method of claim 44 wherein the compound is 4-carboxy-1-(3-methylphenyl)-5-pyrazolecarboxamide or a salt thereof.

* * * * *